(12) United States Patent
Pietrangelo

(10) Patent No.: US 7,718,785 B2
(45) Date of Patent: May 18, 2010

(54) MUTATIONS IN THE SLC40A1 GENE ASSOCIATED TO IMPAIRED IRON HOMEOSTASIS

(76) Inventor: Antonello Pietrangelo, Strada S. Martino Di Mugnano, 3/1, I-41100 Modena (IT)

( * ) Notice: Subject to any disclaimer, the term of this patent is extended or adjusted under 35 U.S.C. 154(b) by 763 days.

(21) Appl. No.: 10/560,157

(22) PCT Filed: Jun. 9, 2004

(86) PCT No.: PCT/EP2004/051068

§ 371 (c)(1),
(2), (4) Date: Jun. 15, 2006

(87) PCT Pub. No.: WO2004/111268

PCT Pub. Date: Dec. 23, 2004

(65) Prior Publication Data

US 2007/0003933 A1    Jan. 4, 2007

(30) Foreign Application Priority Data

Jun. 9, 2003    (IT) .................. MI2003A01156

(51) Int. Cl.
*C12Q 1/68* (2006.01)
*C07H 21/04* (2006.01)
(52) U.S. Cl. .................. 536/23.1; 536/24.3; 435/6; 435/91.1; 435/91.2
(58) Field of Classification Search .......... None
See application file for complete search history.

(56) References Cited

U.S. PATENT DOCUMENTS

| | | | |
|---|---|---|---|
| 6,812,339 B1 * | 11/2004 | Venter et al. | 536/24.31 |
| 2001/0053519 A1 * | 12/2001 | Fodor et al. | 435/6 |
| 2003/0092019 A1 * | 5/2003 | Meyer et al. | 435/6 |
| 2008/0127376 A1 * | 5/2008 | Fincher et al. | 800/312 |

FOREIGN PATENT DOCUMENTS

| | | |
|---|---|---|
| WO | WO 98/32846 | 7/1998 |
| WO | WO/02/33119 | 4/2002 |
| WO | WO 03/002589 | 1/2003 |

OTHER PUBLICATIONS

Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Xu et al. (Genbank Accession No. AV49238, Jan. 2002).*
International Search Report for PCT/EP2004/051068, May 19, 2005.
Montosi et al., 2001 "Autosomal-Dominant Hemochromatosis is Associated with a Mutation in the Ferroportin (SLC11A3) Gene," *The Journal of Clinical Investigation*, 108(4):619-623.
Njajou et al., 2001 "A Mutation in SLC11A3 is Associated with Autosomal Dominant Hemochromatosis," *Nature Genetics*, 28:213-214.
Wallace et al., 2002 "Novel Mutation in *Ferroportin1* is Associated with Autosomal Dominant Hemochromatosis," *Blood*, 100(2):692-694.
European Search Report from 04741762.1, Apr. 2, 2007, Pietrangelo.
Cook et al., 1974, "Serum Ferritin as a Measure of Iron Stores in Normal Subjects," *The American Journal of Clinical Nutrition*, vol. 27:681-687.
Pietrangelo et al., 1999, "Hereditary Hemochromatosis in Adults Without Pathogenic Mutations in the Hemochromotosis Gene," *The New England Journal of Medicine*, vol. 341(10):725-732.
Pietrangelo, A., 2004, "The Ferroportin Disease," *Blood Cells, Molecules, and Diseases*, vol. 32:131-138.
Mougiou et al., 2008, Letter to the Editor, *Blood Cells, Molecules, and Diseases*, vol. 14:138-139.
Wallace and Subramaniam, 2007, "Non-HFE Haemocromatosis," *World Journal of Gastroenterology*, vol. 13(35):4690-4698.

* cited by examiner

*Primary Examiner*—Jeanine A Goldberg
(74) *Attorney, Agent, or Firm*—Jones Day

(57) ABSTRACT

The present invention relates to mutations in the SLC40A1 gene coding for the ferroportin 1, associated to impaired iron homeostasis or to non-HFE hereditary hemochromatosis and to methods for the diagnosis of these hereditary diseases based on the identification of said mutations.

14 Claims, 7 Drawing Sheets

MUTATIONS IN THE SLC40A1 GENE ASSOCIATED TO IMPAIRED IRON HOMEOSTASIS

This application is the national stage of International Application No. PCT/EP2004/051068, filed Jun. 9, 2004, and claims priority of Italian Application No. MI2003A001156, filed Jun. 9, 2003, the contents of which are incorporated by reference herein in their entireties.

FIELD OF INVENTION

The present invention relates to new mutations of the gene coding for Ferroportin 1 associated to a new variant of a genetic disorder characterized by iron accumulation and the identification of said mutations as a diagnostic method for Hereditary Hemochromatosis.

BACKGROUND OF THE INVENTION

Hemochromatosis is a genetic disorder characterized by an excess of iron accumulation in the body, causing in the course of the time injuries in different organs and tissues, particularly in liver, myocardium, pancreas, kidney, spleen, gonads and skin. Idiopathic Hemochromatosis is the most wide-spread hereditary disease in the Western population (incidence 1:300) and it is characterized by a recessive inheritance. This kind of Hemochromatosis was at first associated to HFE gene mutations (Hereditary Hemochromatosis described in Feder et al., Nat. Genet. 1996, 13:399-408). More recent studies have at first supposed and then proved that mainly in South-Western population, other genes in addition to HFE could have a role in Idiopathic Hemochromatosis (Piperno et al, Gastroenterology 1998, 114: 996-1002 and Borot et al, Immunogenetics 1997, 45: 320-324).

Some mutations in the ferroportin gene, recently named SLC40A1 and previously known as SLC11A3 or IREG-1 or MTP-1, have indeed already been identified both by the authors of the present invention and by others as described for instance in Montosi et al., J. Clin. Invest, 2001, 108:619 and In WO 02/033119; Devalia V. et al., Blood, 2002, 100:695; Cazzola et al., British Journal of Hematology 2002, 119:539; Wallace et al., Blood, 2002, 100:692; Njajou Nat. Genet. 2001, 28:213.

The identification of most of the genetic alterations responsible for Hereditary Hemochromatosis or diseases linked to impaired iron homeostasis is of great importance both in diagnostics and therapeutics. In fact, till today the diagnosis of Hemochromatosis is delayed and it is based on clinical symptomatology developed as a consequence of tissue injuries which are frequently irreversible. Moreover the diagnosis of such disease is made difficult by the fact that its symptoms are often similar to those of other diseases characterized by impaired iron homeostasis.

The development of methods of genetic screening for the early diagnosis in a presymptomatic stage, of the Hereditary Hemochromatosis would allow to operate in time by phlebotomy to prevent in this way damages to organs and tissues.

Moreover the identification of genetic alterations linked to Hereditary Hemochromatosis and the comprehension of their role in the development of the pathology, are most relevant for the optimization of new and improved therapeutic strategies.

SUMMARY OF THE INVENTION

The present invention relates to isolated polynucleotides coding for a ferroportin 1 which is mutated in at least one of the positions corresponding to the following aminoacids: position 80, position 174 or position 248 of IDN2 sequence. The identification of said mutations in the protein or in the nucleic acids coding for the protein is extremely useful for the diagnosis and therapy of non-HFE Hemochromatosis, Bantu Siderosis or African Hemochromatosis or for the predisposition to said diseases.

In addition the invention also relates to methods for the molecular diagnosis based on the use of oligonucleotides derived from said sequences or on the use of specific antibodies for said mutations.

Furthermore the invention also includes diagnostic kits for the identification of said polymorphisms.

Panel A shows the relationship among tested subjects (pedigree) in the family carrying the G80 mutation. The subjects affected by Hemochromatosis are indicated in black, whereas the healthy ones are indicated in white. Circles indicate female subjects whereas squares Indicate male subjects.

In panel B is visualized the electropherogram obtained by DNA automatic sequencer on the DNA fragment amplified according to the invention from a control (not carrying the polymorphism) and from affected subject (carrying the polymorphism).

Panel C shows the restriction patterns obtained by enzymatic cleavage with TspR1 of genomic DNA amplified from each subject by the sequencing primers IDN13 and IDN 14.

As shown in panel C, in healthy subjects carrying only the wild type sequence after digestion with TspR1 the amplified DNA of 421 base pairs is not cleaved. In the subjects affected by the disease heterozygous for the mutation, the amplified DNA is digested into a band of 421 base pairs (wild type allele) and two fragments of respectively 238 and 183 base pairs (the latter is not visible in FIG. 1C). (+/+): homozygous subjects for wild type ferroportin, (+/−): heterozygous subjects for the mutation.

Figure 2A:
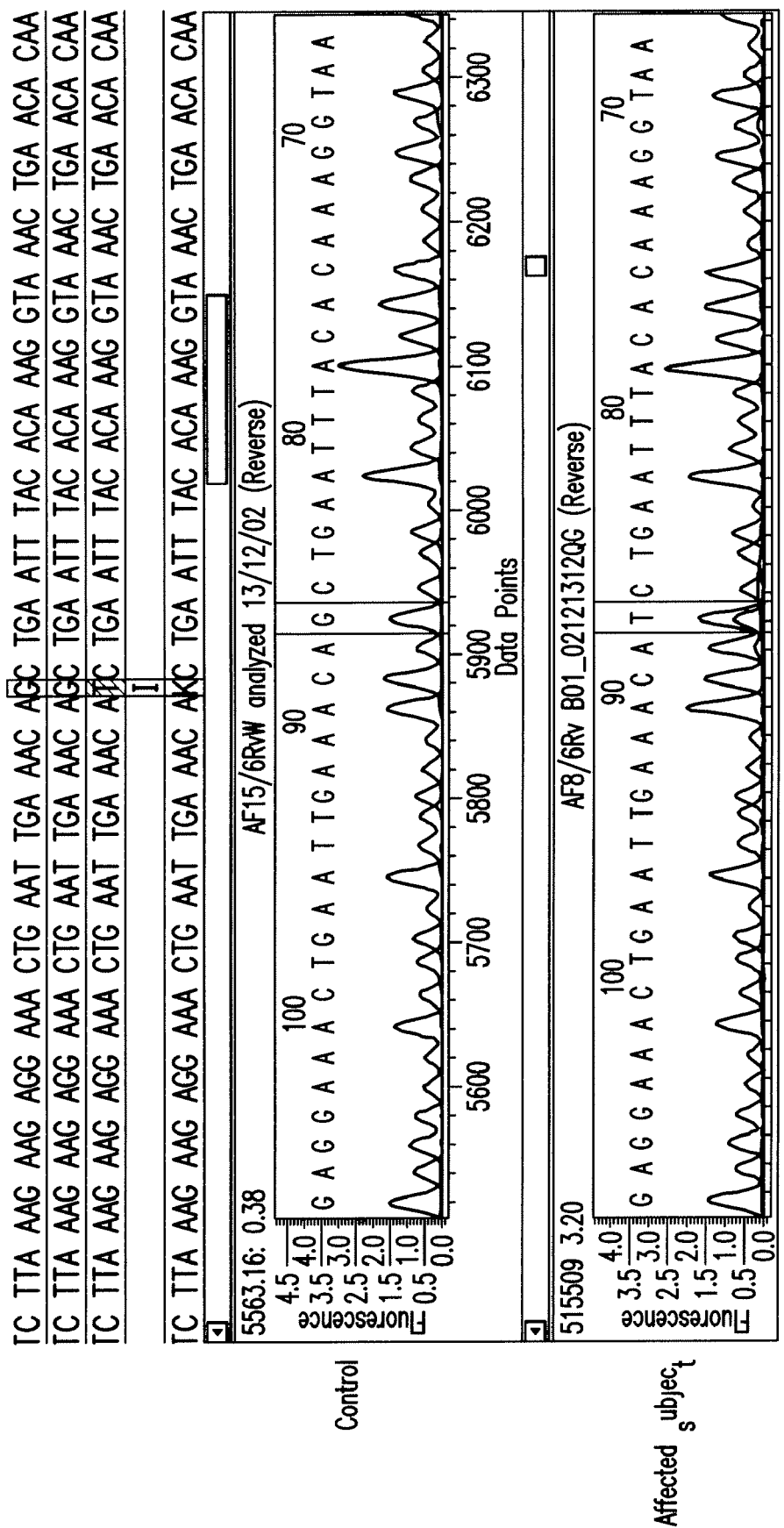
Figure 2B:
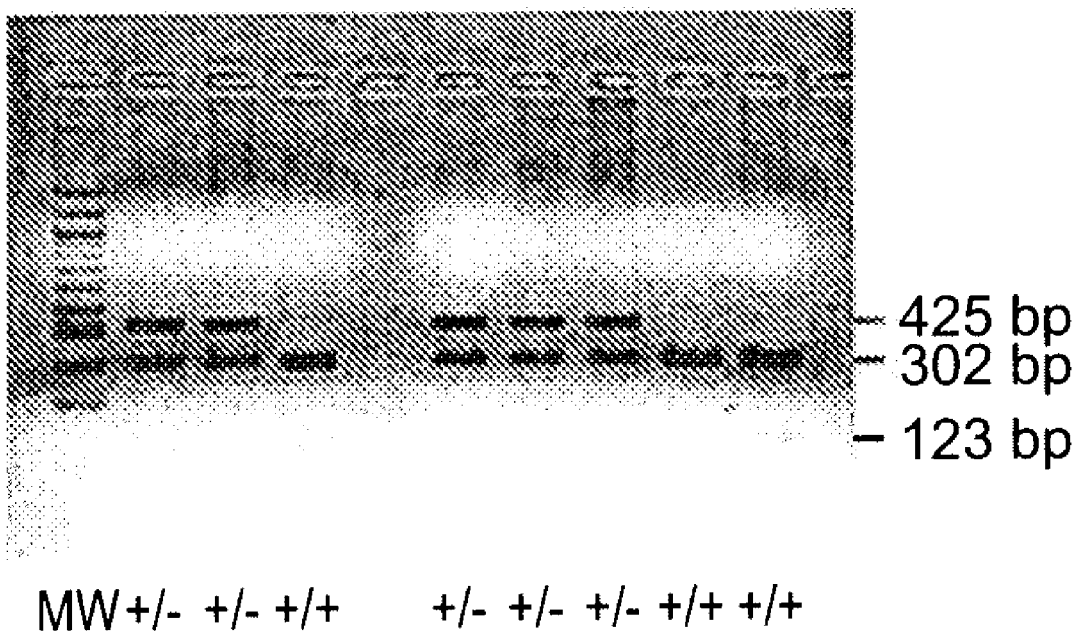

FIG. 2. N174 mutation. Results of the diagnostic analysis of hemochromatosis affected or non-affected family members.

Panel A shows the relationship among tested subjects (pedigree) in the family carrying the N174 mutation. Subjects affected by Hemochromatosis are indicated in black, whereas the healthy ones are indicated in white. Circles indicate female subjects whereas squares indicate male subjects.

In panel B is visualized the electropherogram obtained by DNA automatic sequencer on the DNA fragment amplified according to the invention from a control (not carrying the polymorphism) and from affected subject (carrying the polymorphism).

Panel C shows the restriction patterns obtained by cleavage with BsmI of genomic DNA amplified by the sequencing primers IDN19 and IDN 20 from healthy and affected subjects.

In healthy subjects carrying only the wild type sequence, the amplified DNA of 425 base pairs is digested with BsmI into fragments of respectively 342 and 83 base pairs. In the subjects affected by the disease the polymorphism removes the enzyme target site and as a consequence the amplified DNA is not digested.

As the carrier individuals are heterozygous for the mutation, three different fragments will be obtained by BsmI digestion: a band of 425 bp (mutated allele) and two bands of 342 and 83 base pairs (wild type allele) respectively.

(+/+): homozygous subjects for wild type ferroportin, (+/−): heterozygous subjects for the mutation.

Figure 3A:
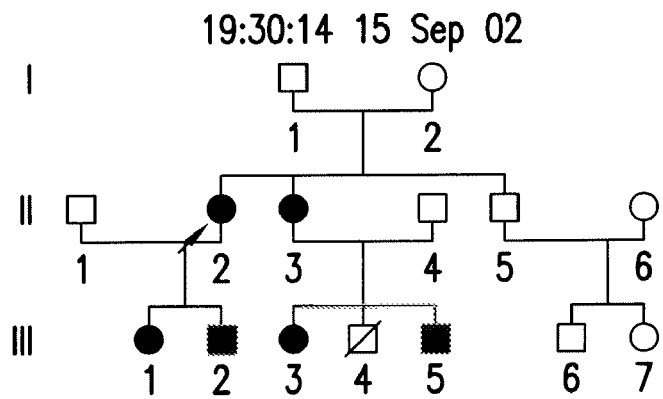
Figure 3B:
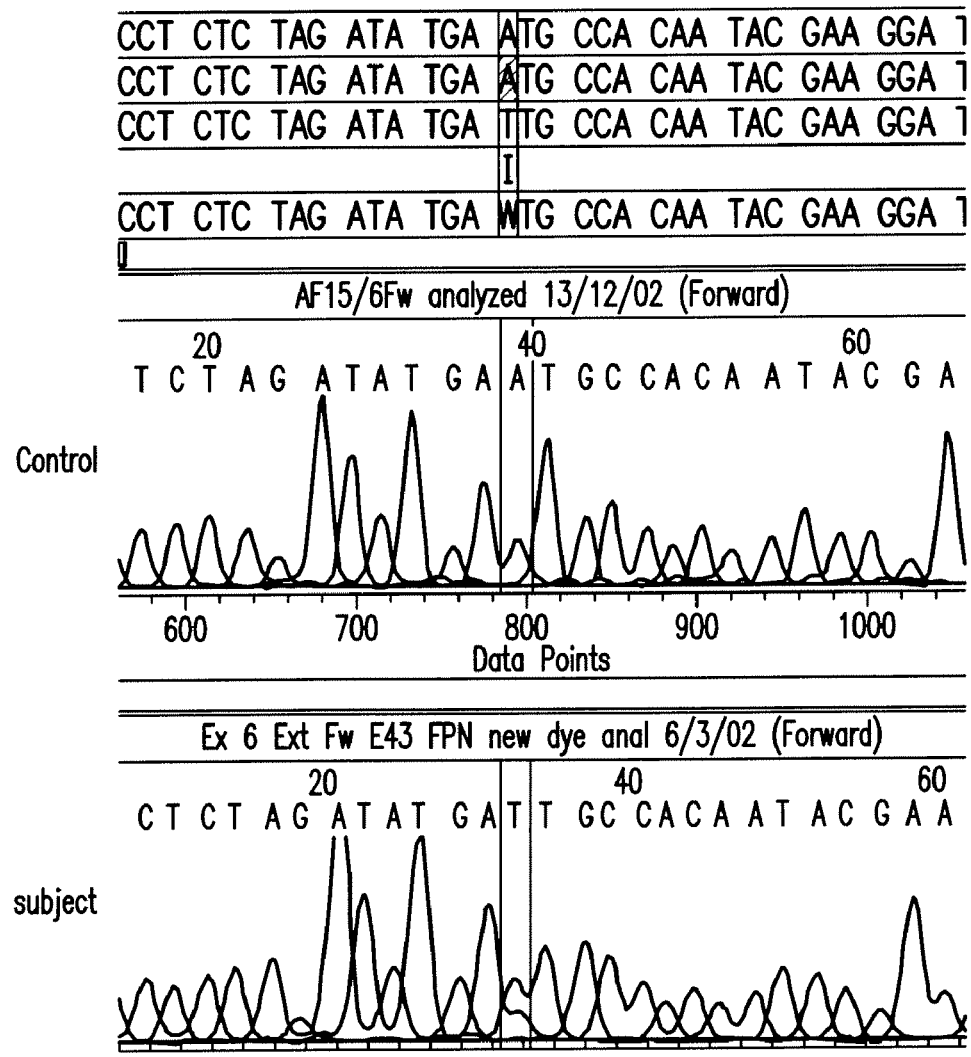
Figure 3C:
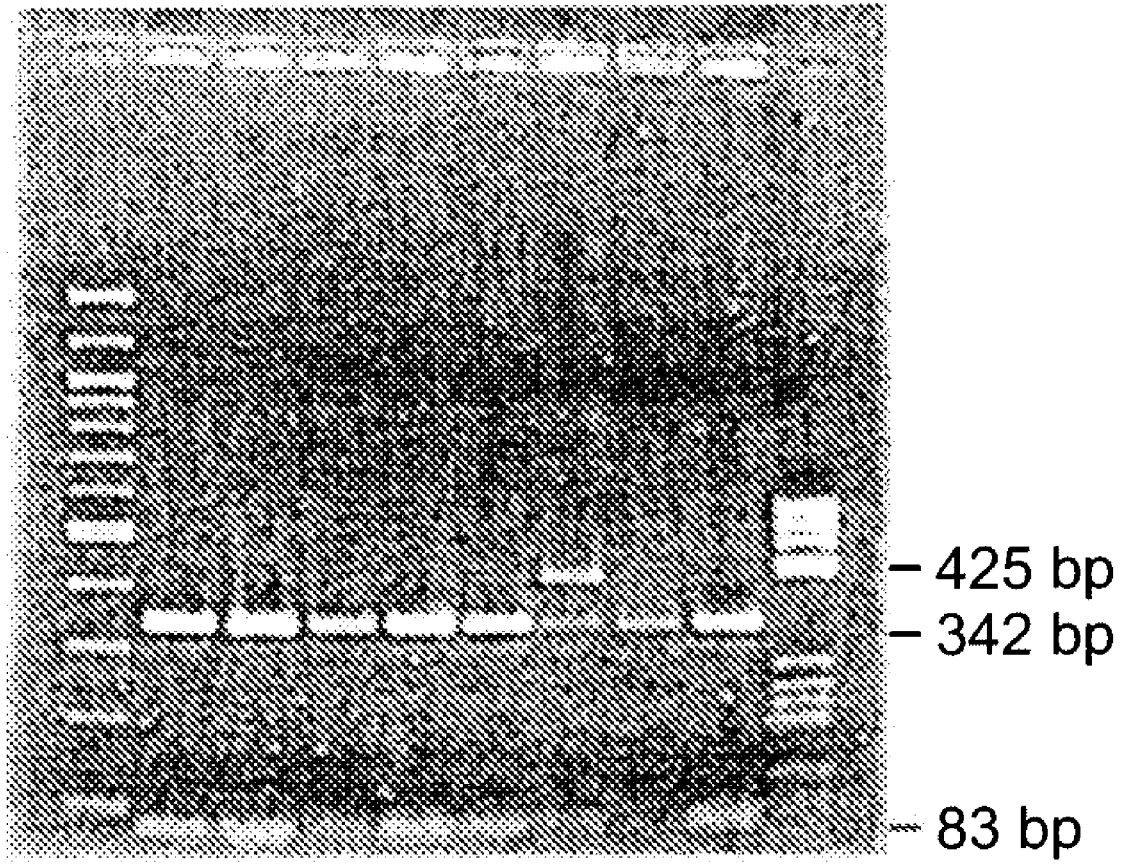

FIG. 3. Q248 mutation. Results of the diagnostic analysis of Bantu Siderosis affected or non-affected family members.

Panel A shows the portion of DNA sequence of exon 6 where it was detected the mutation in African Siderosis subjects and Black Americans.

Panel B shows the restriction pattern obtained by PvuII digestion of the amplified DNA from different subjects with the primers of sequence IDN 19 and IDN 20. As shown in FIG. 3b in healthy subjects carrying only the wild type sequence the amplified DNA of 425 base pairs is digested with PvuII restriction enzyme.

The mutation removes the enzyme cleavage site and only one out of two alleles is digested in a heterozygous subject for the mutation so that three bands will be obtained: a 425 bp band (mutated allele) and two bands of 302 and 123 base pairs (wild type allele) respectively.

(+/+): homozygous subjects for wild type ferroportin, (+/−): heterozygous subjects for the mutation.

DETAILED DESCRIPTION OF THE INVENTION

The authors of the present invention have identified new mutations in the SLC40A1 gene (Solute Carrier Family) coding for ferroportin 1 (IREG1 or MTP1), previously also named SLC11A3, genetically linked to Hereditary Hemochromatosis or to an Impaired non-HFE iron homeostasis (Hereditary Hemochromatosis).

The mutations described in the present invention were detected in the SLC40A1 gene coding for ferroportin, in the codons corresponding to aminoacids G80, N174 and Q248 of ferroportin 1, where said notation is referred to the wild type sequence with accession number NM_014585 (GenBank) and reported in the sequencing listing annex with the identification number 1 (seqIDN1, wild type). At genomic level the mutations are located in the exon 3 (G80 mutation) and in the exon 6 (mutations N174 and Q248) of the SLC40A1.

Said mutations cause aminoacid substitutions in the corresponding protein whose expression as a mutated form causes abnormal iron overload in carrier subjects. From the functional point of view indeed ferroportin has a key role in at least two different but correlated aspects of iron homeostasis: in the enterocytes ferroportin causes the uptake of iron introduced by diet, whereas in the reticular endothelial cells particularly in macrophages, it causes the iron release from intracellular stores. Said new mutations are responsible for the Hemochromatosis and are characterized by clinical traits at least partially similar to those already described in Pietrangelo et al. New England Journal of Medicine 1999, 341 (10): 725-732, caused by the mutation of the aminoacid 77 in the ferroportin sequence (A77D mutation) described In WO 02/033119.

Therefore, a first aspect of the invention refers to polymorphic polynucleotides related to mutated SLC40A1 sequences, which encode for mutated forms of the wild type ferroportin 1 and in particular to at least one of the following polymorphisms:

polymorphism of the nucleotide corresponding to the nucleotide 238 of the IDN 1 sequence, preferably related to the substitution of a Guanine with an Adenosine (G→A), which causes the replacement of aminoacid 80 with an aminoacid different from Glycine and preferably with Serine (G80S) in the coded protein: the cDNA derived from such polymorphic gene has preferably the IDN3 sequence;

polymorphism of the nucleotide corresponding to the nucleotide 521 of the IDN 1 sequence, preferably related to the substitution of an Adenine with a Tymine (A→T), which causes the replacement of aminoacid 174 with an aminoacid different from Asparagine and preferably with Isoleucine (N174I) in the coded protein: the cDNA derived from such polymorphic gene has preferably the IDN5 sequence;

polymorphism of the nucleotide corresponding to the nucleotide 744 of the IDN1 sequence, preferably related to the substitution of a Guanine with a Tymine (G→T), which causes the replacement of amino acid 248 with an amino acid different from Glutamine and preferably with Hystidine (Q248H) in the coded protein: the cDNA derived from such polymorphic gene has preferably the IDN7 sequence;

or their oligonucleotide fragments comprising the polymorphic nucleotide of at least 10 base pairs.

The isolated polynucleotides obtained according to the invention and referred to the notation of the wild type cDNA sequence with GenBank accession number No NM_0145585, as partially reported in sequence IDN1, include at least one of the following substitutions: Guanine at position 552, preferably with Adenine, Adenine at position 835 preferably with Tymine, Guanine at position 1058 preferably with Tymine: this notation is referred to the aforementioned sequence in GenBank.

The oligonucleotides of the invention can be synthetized by chemical or enzymatic methods, or by enzyme digestion of isolated polynucleotides with restriction enzymes.

A preferred embodiment of the polynucleotides are the sequences IDN3, IDN5 and IDN7 or their fragments of at least 10 nucleotides and carrying at least one of the aforementioned polymorphic substitutions wherein the nucleotide sequences correspond to the cDNA coding for each of the mutated ferroportin sequences above described. When the polynucleotide is DNA it can be both single stranded or double stranded DNA, preferably the oligonucleotide is single stranded. Polynucleotides or oligonucleotides according to the invention can include modified nucleotides such as for example the thioderivatives nucleotides.

The invention also includes polynucleotides and oligonucleotides with complementary sequences to polynucleotides and oligonucleotides described in the invention and characterized in that they comprise the complementary nucleotide to at least one of the above described polymorphic nucleotides.

Preferably they are complementary to IDN1, 3 and 5 or their fragments as well as the oligonucleotides of at least 10 base pairs including at least one of the polymorphisms: then, preferably including the nucleotide complementary to the polymorphism at position 238 of IDN1 sequence, or the nucleotide complementary to the polymorphism of the nucleotide at position 521 of IDN1 sequence, or the nucleotide complementary to the polymorphism at position 744 of IDN1 sequence. The polynucleotides and oligonucleotides complementary to the above ferroportin sequence can be used to specifically regulate the expression of the corresponding transcripts o can be used as specific probes to detect the presence of at least one of the aforementioned polymorphisms.

The oligonucleotides and polynucleotides of the invention can also be only partially identical or partially complementary to ferroportin 1 sequences identified as IDN 3, 5, 7 sequences or their fragments and so including non-homologous or non-identical regions. The complementary or homologous region to ferroportin or to its complementary sequence is in this case of at least 10 nucleotides. In particular it is fundamental that the addition of the nucleotides at 5' end or 3' end to the oligonucleotides do not affect the specificity in the detection of the polymorphisms.

Complementary sequences can hybridize to each other under stringent conditions in a specific way. Consequently complementary polynucleotides and oligonucleotides of the invention can specifically hybridize to polynucleotides or to sequences carrying the mutations in the polymorphic sites, in particular to IDN3, 5 or 7 sequences and their fragments or oligonucleotides.

Furthermore the present invention includes oligonucleotides used for the amplification of genomic DNA regions or cDNAs comprising the said mutations. A preferred embodiment is represented by: oligonucleotides of IDN9-22 sequence, used to amplify as pairs genomic DNA of exon regions from 1 to 7 (for example sequencing primers IDN9 and IDN 10 amplify the exon 1, seq IDN 11 and 12 amplify the exon 2 and so on as described in more details in the experimental examples). Particularly preferred are oligonucleotides pairs of sequences IDN 13 and IDN 14 which amplify exon 3 of the genomic DNA, including the polymorphism corresponding to the nucleotide 238 of the sequence IDN1 and IDN19 and IDN20 oligonucleotides pairs which amplify the exon 6 region, including the polymorphisms corresponding to nucleotides 521 and 744 of the sequence IDN1. According to the present invention "nucleotide fragment" or polynucleotide refers to a nucleic acid with a partial sequence of sequences IDN 3, 5 and 7, longer than 50 nucleotides and including at least one of the aforementioned mutations or polymorphisms.

According to the present invention "oligonucleotide" refers to a nucleic acid with a portion of the sequences IDN 3, 5 and 7 and with at least 10 b in length.

According to a further and relevant aspect, the invention also refers to a protein, the ferroportin 1, essentially as an isolated and purified form, having a mutated aminoacidic sequence as compared to the wild type respectively at position corresponding to Glycine 80, or at position corresponding to Asparagine 174 or at position corresponding to Glutamine 248, referred to the aminoacid sequence from the cDNA with accession number NM_014585 (GenBank).

The amino acids notation along the protein have the only purpose to unequivocally identify them, as they can change for example because of the presence of other species-specific mutations or for the presence of insertions or deletions in the DNA region coding for sequences upstream of said amino acid.

The G80S mutation causes the substitution of Glycine, an amino acid of MW 75 and with an intermediate polarity into Serine, an hydrophilic amino acid with MW 105. The N174I mutation causes the substitution of Asparagine, an uncharged hydrophilic amino acid of MW 132 into isoleucine an uncharged hydrophobic amino acid of MW 131. The substitution of the amino acid 174 is of great importance for the protein as it is a putative glycosilation site. The mutation at the position corresponding to the amino acid 248 of ferroportin 1 is a marker of the African variant of Hereditary Hemochromatosis, named African Siderosis, geographically localized in the Sub-Saharian regions and characterized by an excess iron deposition mainly in the reticular endothelial system, with an increase of early ferritinemia, only sometimes associated to a complete saturation of circulating transferrin.

These tracts are surprisingly similar to the ferroportin-associated disease already described (Pietrangelo et al. New England Journal of Medicin 1999, 341(10):725-732).

Some clinical traits associated to the described mutations may be summarized as follows:

i) in the G80S mutation carriers: ferritinemia increases at 1000-2000 ng/ml in untreated males; whereas in females ferritin usually do not exceed 700 ng/ml also in elderly females in a post-menopause age;

ii) in the N174I mutation carriers: it is observable a relevant increase of ferritinemia exceeding 4000 ng/ml also in females. It is likely that the mutation has a more severe effect on the structure and the function of the protein as compared to other mutations.

iii) In the Q248H mutation carriers: It is observable in Black Americans and Africans. Said mutation has an aggravating effect on a pre-existing iron overload condition. In American patients carriers for thalassemia, it causes a more severe phenotype with hyperferritinemia and iron deposition in reticular endothelial cells (macrophages) of liver and bone marrow, a typical trait of the disease as described by the authors of the present invention (Pietrangelo et al 1999) although patients were not subjected to blood transfusion (practice which can cause iron overload in macrophages). In African patients affected by Bantu Siderosis (that is associated to the excessive use of beer produced in iron containers) it is responsible for a higher ferritinemia as compared to that found In patients which do not carry the mutation but drink comparable quantity of alcohol.

Paradoxically, the presence of the mutation also causes anaemia, with a highly significant decrease in the hemoglobin levels.

Furthermore the mutation can be used as a marker of Black African population. In fact, it was not present in any Caucasian healthy donors, but it was found in 6 out of 100 chromosomes of African individuals with a normal phenotype and in four out of 100 Black Americans anonymous donors.

The analysis of the phenotipically healthy individuals showed a trend towards higher levels of ferritinemia and significantly lower hemoglobinemia as compared to non-mutated individuals. Therefore, the mutation in association with other factors (for example thalassemia and/or alcohol consumption) is responsible for a more severe phenotype. In addition in Black African and American populations it might have an effect in causing potentially lower levels of hemoglobin and potentially higher levels of ferritinemia as described more in details in the annotations of Table 1 in the Experimental Examples.

It is however to consider that hemoglobin and ferritinemia values are not by themselves sufficient to provide per se a diagnostic indication of non-HFE Hemochromatosis, but only together with the presence of at least one of the mutations described in the invention. Such values can differ considerably from the above reported data, because of the presence of other factors such as the age of the subject or the time the diagnosis is carried out.

According to a further aspect, the invention comprises peptides or polypeptides longer than 5 amino acids with a portion of sequence corresponding to ferroportin 1 protein sequence and characterized by the presence of mutations in the amino acid positions corresponding to Glycine at position 80, or to Asparagine at position 174 or to Glutamine at position 248. Such peptides or polypeptides are obtained by chemical synthesis or by recombinant techniques. Preferably, polypeptides carrying at least one of the above Identified mutations longer than 100 amino acids are obtained by recombinant DNA techniques, whereas peptides Including at least one of the above identified mutations, shorter than 100 amino acids are preferably obtained by chemical synthesis.

According to the structural prediction described in Davalia et al., G80 and N174 mutations are localized in the ferroportin extracellular domains, whereas the Q248 mutation is the first mutation mapping into an intracellular domain corresponding to amino acids 221-306, according to this prediction.

The domain carrying such mutation is then a further subject of the invention as for the first time it is surprisingly associated to polymorphisms causing clinical traits similar to those described for non-HFE Hereditary Haemochromatosis and able to cause a more severe phenotype when associated to other factors (for example alcohol consumption, Thalassaemia). Obviously the Impairement of ferroportin functionality as a consequence of Q248 mutation is not linked to the assignment to an intra or extracellular domain according to the secondary or tertiary structure prediction model and it is therefore independent to the strength of the prediction model used.

A further aspect of the invention relates to peptides whose sequence derives from seq IDN 2 (or from seq IDN 4 or from seq IDN 6 or from seq IDN 8) with a length of at least 5 amino adds and including the corresponding amino acid at position 80, 174 and 248 of seq IDN 2 (or 4 or 6 or 8) and the amino acid immediately upstream or downstream said mutations. The length and the sequence of said peptides are selected according to criteria known to the person skilled in the art on the basis of the preferred application.

A preferred embodiment of such peptides are the peptides comprising or corresponding to: Ile-Ile-X-Asp-Trp (G80 seq IDN 28) where X is different from Glycine and is preferably Serine; Asn-Met-X-Ala-Thr (N 174 seq IDN 29), where X is different from Asparagine and is preferably isoleucine; Leu-Lys-X-Leu-Asn (Q 248 seq IDN 30), where X is different from Glutamine and is preferably Hystidine; polypeptides comprising said peptides are also included in the present invention. Such polypeptides or peptides are useful for example to detect the presence of the described mutations by competition assays on cells, on cells extracts or on purified proteins or in diagnostic immunoassays.

Said peptides may carry at an N or C terminus, additional amino adds residues non derived from ferroportin sequence and performing a different function, for example "tag" peptides to facilitate the purification step.

By convention and according to the present invention, the term "fragment of polypeptide of the ferroportin protein" refers to a molecule corresponding to a partial sequence of the mutated ferroportin 1 as described above, carrying at least one of said mutations and having a sequence longer than 50 amino acids.

According to the invention the term peptide refers to a molecule whose sequence is a portion of the sequence of the mutated ferroportin 1, and carrying at least one of the said mutation with a length of at least 4 amino acids but shorter or equal to fifty amino acids. The present invention also comprises antibodies able to is recognize in a specific way, as compared to the wild type protein, at least one of the G80, N174, Q248 mutation carrying polypeptides.

Such specific antibodies have a diagnostic application since the presence of the ferroportin carrying at least one of the said mutations is an early diagnostic marker of inherited impaired iron homeostasis disease.

Given the high incidence of non-HFE Hereditary Hemochromatosis in the Italian population (64% of the Italian Hemochromatosis variants) and in the rest of the world where have been described cases in Caucasian, Asiatic and other populations, and its continuous progression, polynucleotides, oligonucleotides, polypeptides or peptides, mutated ferroportin forms including said mutations as well as specific antibodies for the mutations identified in the protein, have an evident application in pharmaceutical, diagnostic and therapeutic areas.

In the diagnostic field nucleotides and polypeptides products of the invention are relevant for the diagnosis of non-HFE Hereditary Hemochromatosis, preferably for African and North American Hemochromatosis, for differential diagnosis of the hereditary or congenital hyperferritinemia, or for the diagnosis of anemia of unknown origin in young women or hyperferritinemia of unknown origin in child and adults.

Particularly in Bantu Hemochromatosis or African Siderosis the diagnosis of Q248 polymorphism is mainly useful to identify the genetic background of a more severe phenotype or the risk to develop phenotype together with other factors (alcohol consumption or Thalassaemia). The Q248 mutation is of great importance to identify the genetic background of an impaired iron homeostasis that in the individuals carrying the polymorphism is associated with a normal level of ferrtinemia but with impaired levels of hemoglobinemia.

In vitro molecular diagnosis, based on the identification of DNA or protein mutation as described in the present invention, and carried out by methods and reagents described in the present invention, allows the early diagnosis of Hereditary Hemochromatosis.

Early diagnosis is necessary for this disease which is asymptomatic until the individual is about 30 years old, and which is now frequently diagnosed only after the appearance of adverse effects caused by iron accumulation in the involved organs (lung, liver, joints, pancreas) occurring when their function is already irreversibly damaged.

Oligonucleotides and polynucleotides including the polymorphism causing the Q248 mutation are also useful as genetic marker for Black African population and are used for the study of the genetic linkage for those disease whose defective genes map on the same chromosome.

Nucleic acids of the invention are useful in the therapeutic area particularly in substitutive genetic therapy, where by homologous recombination with wild type sequences and/or for cell therapy they are the target of said sequences.

In fact as the presence in an individual of the gene carrying at least one of the mutations of the invention and the corresponding product (mutated ferroportin 1) is correlated with the outbreak of Hereditary Hemochromatosis, it is of great importance to have the instruments to knock out the expression of the gene or to inactivate the protein. The invention refers then to pharmaceutical compositions including said oligonucleotides, antibodies or peptides mixed with pharmaceutically acceptable excipients.

In one of the most common applications the nucleic acids of the invention, preferably the oligonucleotides shorter than 50 bp, preferably of at least 40 bp or more preferably with the length between 8 and 25, or 8 and 15 nucleotides are used to assay the presence of said polymorphisms in a biological sample.

However the present invention also refers to the therapeutic use of polynucleotides and oligonucleotides of the invention. Typically said oligonucleotides include the aforementioned polymorphism or they have complementary sequence to the region comprising said polymorphism and they are therefore allele specific oligonucleotides and polynucleotides.

Preferably oligonucleotides or nucleic acids or the invention include the following decamers or the corresponding complementary sequences: 5' ATCAGTGACT 3' SEQ ID NO:25 including the underlined polymorphism and responsible for the G80S mutation, 5' GATGATTGCC 3' SEQ ID NO:26 including underlined polymorphism and responsible for the mutation N1741, 5' GAAACATCTG 3' SEQ ID NO:27 including underlined polymorphism and responsible for the mutation Q248H. Therefore they can include additional nucleotides at 5' and at 3' ends only if these do not affect the binding specificity, for example by hybridization to a ferroportin sequence, for the polymorphisms whose therapeutic and diagnostic importance is herein described as a subject of the present invention.

Polynucleotides of the invention, particularly IDN3, 5, 7 or their fragments can also be used for the production of recombinant ferroportin 1 molecules or chimeric proteins or truncated forms of the protein including at least one of the mutated amino acids at position G80, N174, Q248. They are inserted into expression vectors and used to transform prokaryotic and eukaryotic cells according to art-known techniques such as for example, transfection, transformation, Infection or intranuclear injection. Vectors suitable to this aim include, for example, plasmids, viral vectors and yeast or mammalian artificial chromosomes.

According to a further application, the invention refers therefore to a recombinant vector carrying a nucleic acid or a DNA fragment according to the invention as well as to eukaryotic or prokaryotic cells transformed with said vectors. The person skilled in the art is able to choose each time fragment and oligonucleotides with sequences and length suitable to the preferred use. For example, if the fragments or oligonucleotides are used for the identification of a mutation described in the invention by hybridization techniques their length and sequence is chosen to get a specific hybridization under stringent conditions to a nucleic acid sequence including the mutated codon.

Allele-specific oligonucleotide probes are longer than 10 nucleotides, preferably between 15 and 50 nucleotides and more preferably not longer than 35 nucleotides, preferably with a length comprised from 15 to 30 nucleotides. The sequence of such probes is chosen by the person skilled in the art who select them on the basis of the full length sequence also by the use of known software and according to the assay they will be used in. Preferably they include at least one of the oligonucleotide sequences IDN23 IDN24 or IDN25 which are characterized by the fact to comprise at least one of the nucleotide 238, 521 and 744 polymorphisms, according to the sequence notation of IDN1.

The fragments and oligonucleotides of the invention can be labelled, for example with one or more markers chosen among radioisotopes, enzymes, biotine-avidine or other fluorescent molecules able to detect them by specific assays.

According to a further aspect the invention relates to oligonucleotides and polynucleotides characterized by comprising the above described polymorphisms or nucleic acids complementary to them, as well as peptides and proteins corresponding to the mutated ferroportin form for therapeutic use.

Then, due to the importance and incidence of Hereditary Hemochromatosis the invention includes all the nucleic acids and proteins of the invention for therapeutic use. According to a preferred aspect the invention relates to nucleic acids with sequence IDN 3, 5 and 7 and their fragments, the oligonucleotides with the sequences IDN 23-25 and those complementary to them, proteins with sequences IDN 4, 6, 8 and their derived peptides including the amino acid substitution derived from the polymorphism, for therapeutic use.

The polynucleotides according to the invention can also be used for cells and non-human transgenic mammals preparations including the transgene coding for at least one of the mutated forms of ferroportin 1 of the invention. The transgene can be stably inserted in the genome of the animal cell or it can be present as a transient form.

Said non human cells, tissues or animals are useful as models for the study of gene and protein function including the mutations according to the invention and of their role in the outbreak of the Hereditary Hemochromatosis. These models are particularly important for the development of new therapeutic approaches for the treatment of non HFE-Hereditary Hemochromatosis or of the impaired iron overload homeostasis.

In a further aspect the invention refers to a method for in vitro diagnosis of non HFE-Hereditary Hemochromatosis, or African Siderosis or Bantu Hemochromatosis in a mammal, preferably *Homo Sapiens* also in cases where the only detectable clinical trait is only hyperferritinemia or anemia and including the following steps:

a) isolation of nucleic acids contained in a biological sample obtained by said mammal;

b) test for the presence of the mutations or polymorphism according to the invention in said nucleic acid, where the presence of at least one of said mutations or polymorphisms is an intermediate indication that said mammal is affected by a hereditary defect in the regulation of iron homeostasis, or he may be affected by non-HFE Hereditary Hemochromatosis, African Siderosis, hereditary anemia with hyperferritinemia or hereditary disease associated to iron overload in reticular endothelial cells.

Preferably said biological sample is a sample of plasma, saliva, urine, faeces, amniotic liquid or tissue or it consists of cells from biopsies. Preferably said nucleic acid is genomic DNA or RNA. If the nucleic acid is RNA it is preferably transformed into complementary DNA (cDNA) by a reverse transcription reaction. Genomic DNA or cDNA are directly analyzed or after in vitro amplification by polymerase chain reaction (PCR) (Salki et al., Science 239:487-491, 1988) or other techniques such as, for example, ligase chain reaction (LCR) (Wu et al., Genomics 4:560-569, 1989) strand displacement amplification (SDA) (Walker et al., PNAs USA 89:392-396) or self-sustained sequence replication (3SR) (Fahy et al., PCR Methods Appl 1: 25-33, 1992). Preferably genomic DNA or cDNA is amplified by PCR using a pair of oligonucleotides suitable for the amplification of the DNA fragment including the codon coding for the amino acid corresponding to position 80 or 174 or 248 of seq IDN 2.

Oligonucleotide pairs suitable for the amplification of the region containing the mutation G80 on genomic DNA and whose sequence corresponds to sequences IDN13 and IDN 14 can also amplify exon 3. Oligonuclotides suitable for the amplification of the region including N174 and Q248 mutations on exon 6 refers to sequences IDN19 and IDN 20. Oligonucleotides of sequence IDN 9-22 are therefore comprised in the present invention. Particularly preferred is the oligonucleotide pair suitable to amplify the region of the exon 3 comprising the polymorphism responsible for the G80 mutation, that is the pairs consisting of IDN13 and IDN 14 and the oligonucleotide pairs that amplify the region of the axon 6 including the polymorphism responsible for the 0248 mutation and the polymorphism responsible for N174 mutation such as the oligonucleotides pairs consisting of sequences IDN19 and IDN20. Oligonucleotides specific for the axon carrying the mutation can be identified on the genomic DNA sequence close to the sequences identified by said oligonucleotides. The present invention comprises also oligonucleotides carrying at least 8 consecutive nucleotides each oligonucleotide with sequence IDN 9-22, preferably with sequence IDN13 from 14 and from 19 to 20.

Several art-known techniques can be used to identify the presence of mutations according to the invention in genomic DNA or cDNA.

Proper techniques for example are based on the use of restriction enzymes (Kan et al, Lancet: 910-912, 1978), techniques of hybridization with allele-specific oligonucleotide probes (Wallace et al, Nucl Acids Res 6: 3543-3557, 1978) as for example hybridization with oligonucleotides immobilized on filters (Salki et al, PNAS USA 86: 6230-6234, 1989) or micro-chips (Chee et al, Science 274:610-614, 1996) and *oligonucleotide arrays* (Maskos et al, Nucl Acids Res 21: 2269-2270, 1993), allele-specific PCR (Newton et al. Nucl Add Res 17:2503-2516, 1989), *mismatch repair detection (MRD)* (Faham a Cox Genome Res: 474-482, 1995), *Single-strand conformational polymorphism analysis* (Ravnik-Glavac et al, Hum. Mol. Gen. 3: 801, 1994), gel electrophoresis on denaturing gradient (Guldberg et al., Nucl. Acids Res. 22: 880, 1994), *Hot Cleavage* (Cotton et al. Proc. Natl. Acad Sci USA 85: 4397, 1988), *DNAse* (Youil et al, PNAS USA 92: 87-91, 1995) and *RNAse protection assay* (Winter et al. Proc. Natl. Acad. Sci. USA, 82: 7575, 1985; Meyers et al., Science 230: 1242, 1985), *allele specific primer extension* (Syvanen et al, Genomics 8: 684-692, 1990 and Syvanen et al, Hum Mutat 13:1-10, 1999), *genetic bit analysis* (GBA) (Nikiforov et al Nucl Acid Res 22:4167-4175, 1994), *primer-ligation assay* (OLA) (Landergen et al, Science 241: 1077, 1988), *allele specific ligation chain reaction* (LCR) (Barrany PNAS USA 88:189-193, 1991), *gap-LCR* (Abravaya et al Nucl Acids Res 23: 675-682, 1995), sequencing techniques, or Ligase Detection Reaction (described in U.S. Pat. No. 6,312,892).

Particularly preferred techniques for the identification of the mutation of the invention are based on the use of restriction enzymes cutting only in the presence of the aforementioned polymorphism, or allele-specific PCR, or hybridization, or direct sequencing or "computer readable" micro arrays.

Furthermore according to a preferred embodiment the control for the presence of the mutation according to the invention in the DNA to be analyzed, is performed by using techniques based on the use of restriction enzymes and comprising the following steps:

a) amplification of genomic DNA or cDNA with an oligonucleotides pairs suitable for the selective amplification of the fragment of said DNA comprising the codon coding for the amino acid corresponding to position G80 or N174 or Q248, where preferably such amplification occurs with the oligonucleotide pair 13 and 14 for mutation In axon 3 (G80) and the oligonucleotide pair 19 and 20 for mutation in axon 6 (N174 and Q248);

b) incubation of the amplified DNA with a restriction enzyme able to recognize the restriction site modified (produced or removed) by the mutation.

c) analysis of the products size of said digestion and optionally comparison with the restriction pattern obtained from a healthy donor, where the presence or the absence of enzymatic digestion in at least a chromosomic allele indicate the presence in the analyzed individuals of at least one of the mutations responsible for non-HFE Hereditary Hemochromatosis.

The analysis of the size of the products after digestion is performed for example by gel electrophoresis by the use of a molecular weight marker, followed by visualization of the DNA bands for example by ethidium bromide.

As it will be shown in details in the Experimental Examples describing one of the preferred embodiment of the diagnostic method of the invention, the polymorphism of the nucleotide at position 238 (G→A) which causes the substitution G80S in the corresponding protein also generates the restriction site for the enzyme TspRI: the 421 bp fragment amplified with primers of sequence IDN13 and 14 (exon 3), is digested only when the polymorphism is present, in two bands of 238 and 183 bp, whereas it is not affected in the wild type. The presence of the polymorphism of the nucleotide 521 (A→T) which causes the substitution N174I in the corresponding protein is detected after amplification of genomic DNA with the primer pair corresponding to exon 6 (seq ADN 19 and 20), by digestion with BsmI. The polymorphism causes the loss of the recognizing sequence for the restriction site and therefor after DNA amplification and digestion the whole fragment of 425 bp is detected: in the normal individual (wild type), indeed the amplified DNA is digested into two fragments of 342 and 83 bp.

The presence of the polymorphism G→T at position 744 of seq IDN1, causing the substitution Q248H in the corresponding protein, is detectable after amplification of the exon region of 425 bp with the primers pair of sequence IDN19 and 20 (exon 6) by digestion with PvuII: the mutated sequence removes the restriction site of the enzyme and a band of 425 bp is detected, whereas the presence of the wild type allele is detectable as a band of 305 bp and a band of 123 bp.

Aforementioned polymorphisms can be detected throughout the loss or gain of said restriction sites, by selecting suitable primers for the amplification also on the cDNA.

According to a further embodiment the identification of the mutations of the invention is performed by hybridization techniques where nucleic acid fragments of the invention or oligonucleotides specific for the mutation of the invention are used. Said fragments or oligonucleotides are able to specifically hybridize to a sequence of the nucleic acid of the invention including the mutated codon also when said sequence is present together with several other non mutated sequences.

The man skilled in the art is able to select each time the hybridization conditions, the length and the specific sequence of the fragments or of oligonucleotides more suitable to the specific hybridization technique used and to the kind of DNA under evaluation (genomic or complementary DNA amplified or cloned into suitable vectors).

The method to detect the polymorphisms described in the invention is of diagnostic importance to detect the genetic background of iron impaired homeostasis where such iron impaired homeostasis can bring to both anemia and hyperferritinemia. In particular Q248H polymorphismis is of diagnostic importance to detect the genetic background of the disease identified as African or Bantu Siderosis or of a simple anemia.

According to a further preferred embodiment the diagnostic method relates to the use of an allele-specific PCR where the genomic or complementary DNA is subjected to a PCR reaction where oligonucleotides able to selectively amplify a fragment of said DNA comprising the mutated codon but not the corresponding fragment carrying the non mutated codon are used.

In a particularly preferred embodiment the oligonucleotides of the invention used to detect the presence of at least one of the described polymorphisms of the invention are chemically linked to a solid support preferably of glass or to microchips (bidimentional or spherical as the "beads"), which are "computer readable", are preferably arranged as a matrix (array system) and are characterized by the fact to comprise at least one of the polymorphisms of the invention or at least one of the oligonucleotides or polynucleotides of the invention.

Furthermore the present invention comprises diagnostic kits for the diagnosis of the genetic background associated to an impaired iron homeostasis caused by the aforementioned polymorphisms, associated or not to hyperferritinemia or to anemia based on the DNA molecular analysis. Said kits are characterized by comprising at least one of the oligonucleotides or polynucleotides of the invention, detecting the polymorphisms subject of the present invention. According to particularly preferred embodiment said diagnostic kits comprise the oligonucleotides pairs for the amplification of exon 3 (seq IDN13 and 14) and the oligonucleotide pairs for the amplification of axon 6 (seq IDN19 and 20), and the enzymes TspR1 and BsmI and PvuII. As an alternative said kits also include polynucleotides comprising oligonucleotides of sequence IDN25, 26 or 27. Moreover, said kits can possibly include also oligonucleotides and the restriction enzyme to detect the A77D mutation caused by the polymorphism described in the patent application WO 02/33119.

The present invention also refers to a method for the in vitro diagnosis of Hereditary Hemochromatosis in a mammal, including the evaluation of the presence in a biological sample of said mammal, the presence of a mutated ferroportin 1 protein according to the invention, where the identification of said protein is an indication that the individual is affected by Hereditary Hemochromatosis.

Preferably said test is performed by immunological assays using monoclonal or polyclonal antibodies able to discriminate between a mutated ferroportin molecule according to the invention and a wild type ferroportin molecule.

Therefore, the present invention also refers to monoclonal and polyclonal is antibodies able to specifically recognize a mutated ferroportin molecule according to the invention or a peptide or an epitope comprising the mutation. Such antibodies are obtained by art-known techniques such as, for example, the methods described by Harlow and Lane in Antibodies, A Laboratory Manual, Cold Spring Harbour Laboratory, 1988.

Antibodies of the invention are particularly useful as diagnostic reagents but also to study protein features or for therapeutic approaches. For example, said antibodies can be used to detect the tissue or cell localization of the mutated proteins or to study its biochemical characteristics or to purify it by immunoaffinity assay.

Therefore are also comprised in the present invention kits for the study of the function of mutated ferroportin forms based on immunospecific identification of mutated ferroportin forms, preferably Including antibodies specific for G80S, N174I, Q248H mutations and optionally peptides or mutated proteins standards expressed as recombinant products and optionally peptides able to compete with the ligand, for the setting up of ELISA assays or Western Blot, or radioimmunoprecipitation assays on fluid or solid phase.

EXPERIMENTAL EXAMPLES

Example 1

Identification of the Mutations in the Ferroportin Gene

Genomic DNA of index cases, of family members and of control subjects, was extracted from leucocytes obtained by blood samples using a blood DNA extraction kit (Quiagen).

Obtained DNA was then amplified by PCR using primers pair able to amply the whole coding region including exon/intron boundary regions of the ferroportin.

Primers pairs used herein are the following:

```
Exon 1:
Fw.1:  5'-GGTGCTATCTCCAGTTCCTT-3'      (IDN 9)

Rv.1:  5'-GTTCACAGCAGAGCCACATT-3'      (IDN 10)

Exon 2:
Fw.2:  5'-CAGCTCATTAAGTGACTACCATCGC-3' (IDN 11)

Rv.2:  5'-GGCTTAATACAACTGGCTAGAACG-3'  (IDN 12)

Exon 3:
Fw.3:  5'-CATAATGTAGCCAGGAAGTGCCC-3'   (IDN 13)

Rv.3:  5'-TCCAGAGGTGGTGCCATCTAAG-3'    (IDN 14)

Exon 4:
Fw.4:  5'-GAGACATTTTGATGTAATGTACAC-3'  (IDN 15)

Rv.4:  5'-CTACCAGATATTCAATTTTCTGCC-3'  (IDN 16)

Exon 5:
Fw.5:  5'-CCACCAAAGACTATTTTAAACTGC-3'  (IDN 17)

Rv.5:  5'-TCACCACCGATTTAAAGTGAATCC-3'  (IDN 18)

Exon 6:
Fw.6:  5'-GTATTGTGTAAATGGGCAGTCTC-3'   (IDN 19)

Rv.6:  5'-CCCCACTGGTAATAATAAAACCTG-3'  (IDN 20)

Exon 7:
Fw.7:  5'-GGCTTTTATTTCTACATGTCCTCC-3'  (IDN 21)

Rv.7:  5'-ACATTTAGGGAACATTTCAGATC-3'   (IDN 22)

Exon 8:
Fw.8:  5'-AAGGTGACTTAAAGACAGTCAGGC-3'  (IDN 23)

Rv.8:  5'-GCTGACTTAGGTTTCCTAAACAGC-3'  (IDN 24)
```

The amplification of the regions corresponding to each exon was performed as follows: 200 ng of genomic DNA were amplified in 50 µl of reaction buffer 1× containing dNTPs 200 µM, MgCl2 1.5 mM, 25 pmoles of each of the aforementioned oligonucleotides, 1 U of Taq polymerase (Applied Biosystems).

In the amplification reaction was used a program of 30 cycles, each characterized by the following thermal profile:

94° C. for 1 minute,

58° C. for 40 seconds,

75° C. for 5 minutes.

Obtained fragments were purified and sequenced by automatic sequencing with the Backman Coulter Sequencer. The sequence analysis allowed the identification of the G80S mutation in the exon 3 and the N174I and Q248H mutations in the exon 6, as compared to the wild type sequence (GenBank accession number; AF231121) that was not detected in any of the control subjects.

A further evaluation of the mutations was performed by the digestion of an aliquote of the same first PCR product with endonucleases whose restriction site is modified by the nucleotide substitution.

In particular, the Q248H mutation was verified by digestion according to the Manufacturers Instructions (New England Biolabs), the first product of PCR with the PvuII enzyme, which cut into GC in the 5'CAGCTG 3' sequence.

The G→T base substitution in the mutated sequence removes the restriction site of the enzyme.

Example 2

Characterization of Clinical Features of the Subjects Carrying Q248H Mutation

The clinical features of African normal control or Bantu Siderosis affected subjects (associated to excess beer consumption produced into iron containers) carrying the Q248H mutation was evaluated. In said subjects the mutation correlates with higher hyperferritinemia as compared to those subjects without the mutation, but drinking comparable quantity of alcohol.

Paradoxically the presence of said mutation also causes an anemia status with highly significant decrease of hemoglobin. Then, the mutation has an aggravating effect on a preexisting status of iron overload.

In Black American patients carriers for thalassaemia, the mutation causes a more severe phenotype with hyperferritinemia and iron deposition in reticular endothelial cells (macrophages) of liver and bone marrow, although patients were not subjected to blood transfusions (practice which can cause iron overload in macrophages). Hyperferritinemia and iron accumulation in reticular endothelial cells correspond to the clinical features observed by the same authors of the present invention in Pietrangelo et al.; 1999 N. Engl. J. Med 3341: 725-732.

Moreover the mutation is a marker of Black African population: it resulted in fact absent in a sample of 300 healthy White Caucasian donors.

In African population 100 chromosomes from phenotipically normal African subjects were assayed and 6 out of such chromosomes carried the mutation. Similarly, the mutation was found in 4 out of 100 of a group of Black American donors. The analysis of these phenotipically healthy subjects showed a trend towards higher levels of ferritinemia and significantly lower hemoglobinemia as compared to non-mutated individuals. Then the mutation is not able to cause a disease, but it is responsible for a more severe phenotype in association with other factors (for example thalassaemia and alcohol consumption). In addition in Black African and American populations it might have an effect in causing potentially lower hemoglobin levels and potentially higher ferritinemia levels. These conclusions also arise from Table 1 of the Experimental Examples where are reported data concerning ferritinemia and hemoglobin in patients carrying the mutation in Africans, Americans and in phenotipically healthy Black populations.

TABLE 1

Evaluation of the "Iron status" and of the hemoglobin levels in the Q248H ferroportin mutation in Africans and Afro-Americans. The members of the families come from three African and one Afro-American pedigress. The number of individuals in each group is indicated under each parameter (N =).

| | Ferroportin Q248H mutation | Ferroportin wild type | p |
|---|---|---|---|
| Families Members (affected cases are not included) | (N = 10) | (N = 11) | |
| Ferritin (µg/L; mean and SE range) | 76(47–125) | 95(62–147) | 0.748 |
| Ferritin/AST ratio* (µg/U; mean ± SE) | 14.7 ± 4.6 | 5.5 ± 4.1 | 0.171 |
| Transferrin Saturation (%; mean ± SE) | 36 ± 7 | 22 ± 8 | 0.258 |
| Hemoglobin*** (g/dL; mean ± SE) | 11.8 ± 0.6 | 13.3 ± 0.5 | 0.088 |
| Normal Africans | (N = 7) | (N = 44) | |
| Ferritin (µg/L; mean and SE range) | 61(38–97) | 34(28–40) | 0.251 |
| Transferrin Saturation (%; mean ± SE) | 28 ± 5 | 26 ± 2 | 0.684 |
| Hemoglobin (g/dL; mean ± SE) | 12.5 ± 0.5 | 13.7 ± 0.2 | 0.039 |
| Families members and combined controls | (N = 17) | (N = 55) | |
| Ferritin/AST ratio (µg/U; mean ± SE range) | 61(44–82) | 44(37–51) | 0.358 |
| Transferrin Saturation (%; mean ± SE) | 30 ± 4 | 26 ± 2 | 0.357 |
| Hemoglobin (g/dL; mean ± SE) | 12.1 ± 0.4 | 13.6 ± 0.2 | <0.0005 |

Statistical analysis was performed by the ANOVA test adjusted for the age, gender and for Africans, for beer consumption. In the screening pilot study of Q248H mutation were included the family members of patients with iron overload (N=21) and African subjects with normal values of iron metabolism. It is evident in said "normal" population that the presence of Q248H mutation is associated to a trend to an increase of ferritin levels and particularly to a significant decrease of hemoglobin.

Example 3

Set Up of the Diagnostic Method by PCR

By the sequencing of exons regions amplified as described in the EXAMPLE 1, it was evident that the polymorphism of 238 nucleoide of the IDN1 sequence, consisting on the substitution of a Guanine by an Adenine (G→A) responsible of the substitution of the Glycine at position 80 of IDN2 sequence by a Serine (G80S) in the corresponding coded protein, causes the generation of a cleavage site for TspR1 enzyme.

Figure 1A:
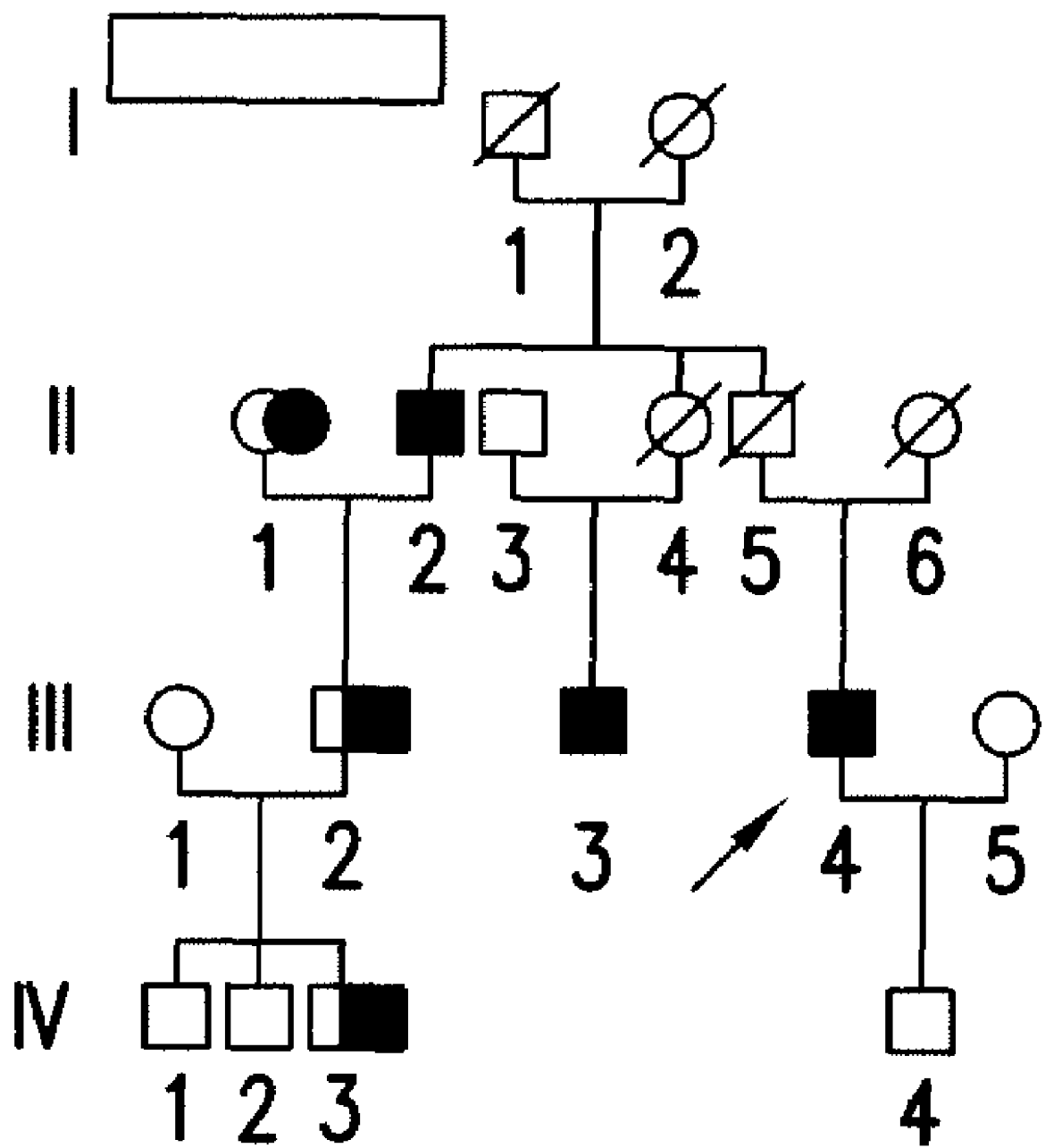
FIG. 1: G80 mutation. Results of the diagnostic analysis of Hemochromatosis affected or non-affected family members.
Figure 1B:
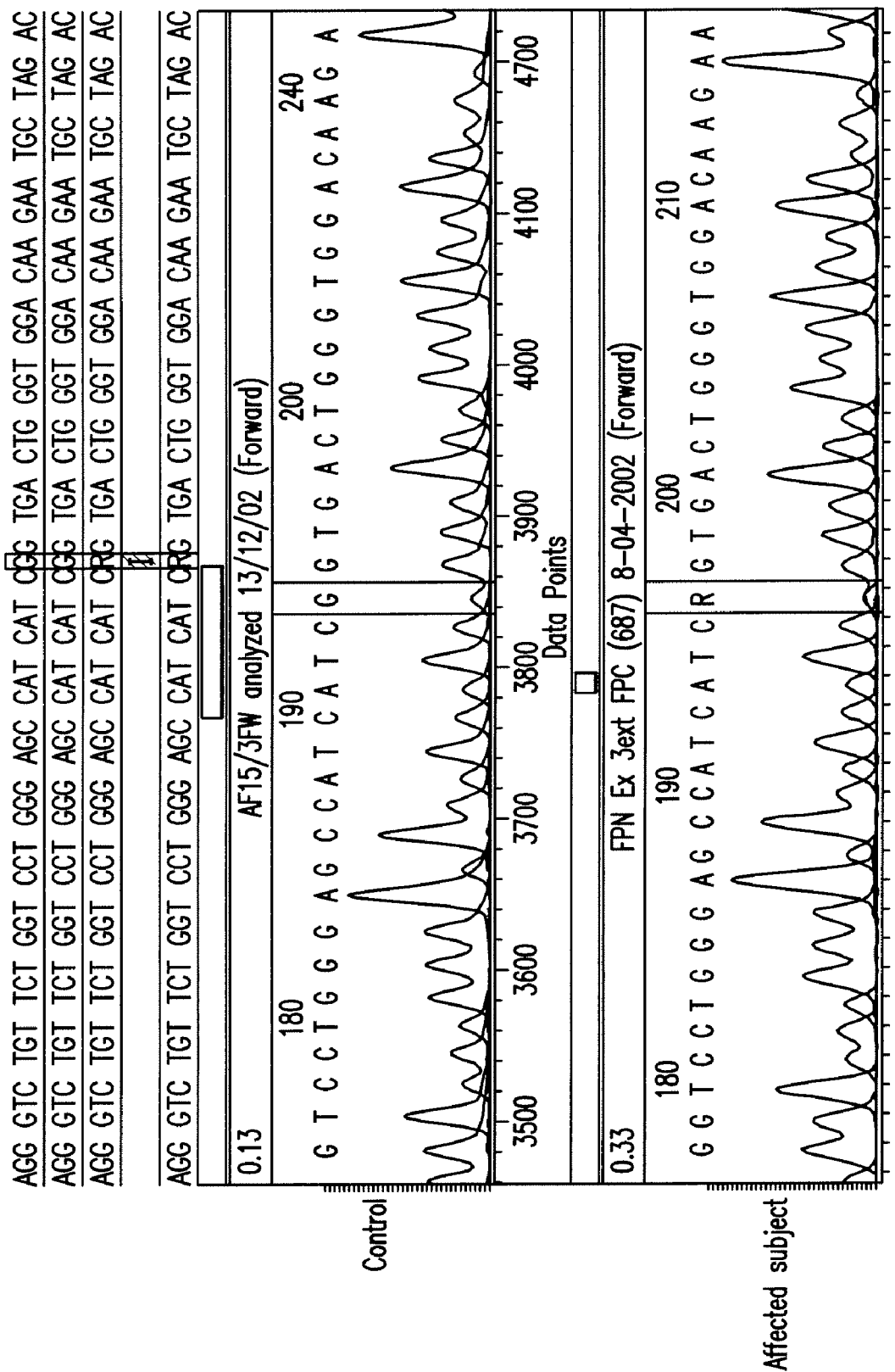
Figure 1C:
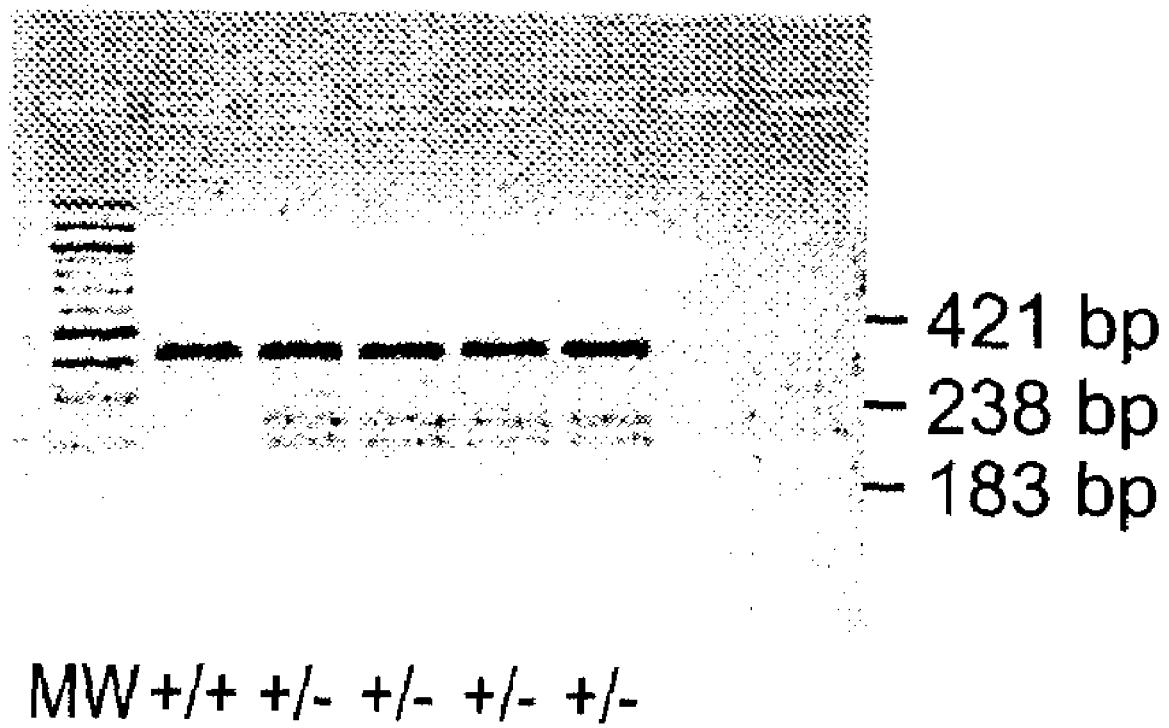

The sequence of the full length cDNA coding for the mutated form of ferroportin at position 80 (G80S) is reported as SEQ ID NO:3 in the sequences listing annex. FIG. 1C show the restriction pattern of the amplified genomic DNA of each individual: in the healthy subjects having only the wild type sequence, after digestion with Tspr1 the fragment of amplified DNA with the oligonucleotide pairs 13 and 14, of 421 base pairs, is not cleaved.

In affected subjects, heterozygous for the mutation, the amplified DNA is cleaved into a band of 421 base pairs (wild type allele) and two bands of 238 and 183 base pairs (this last not visible in FIG. 1C.

The polymorphism of nucleotide 521 of IDN1 sequence, consisting in the substitution of an Adenine by a Tymine (A→T), causing the substitution of Asparagine with an isoleucine at position 174 (N174I) in the corresponding coded protein, whereas it causes the knock out of the cleavage site for the restriction enzyme BsmI and as a consequence the DNA fragment of exon 6 from individuals carrying the polymorphisms amplified by oligonucleotide pairs 19 and 20 is not cleaved. The sequence of the full length cDNA coding for the mutated form of ferroportin at position 174 (N174I) is reported as IDN5 sequence in the sequencing listing annex. FIG. 2 panel B shows the restriction pattern obtained after digestion with BsmI of amplified DNA from healthy individuals carrying the polymorphism. In case of healthy subjects having only the wild type sequence, after digestion with BsmI of the DNA fragment of 425 bp amplified with primer pairs 19 and 20, it is digested into two fragments of 342 and 83 base pairs. In carriers subjects, heterozygous for the mutation, after digestion with BsmI three bands were visualized: a band of 425 base pairs (mutated allele) and two bands of 342 and 83 base pairs (wild type allele).

The polymorphism of nucleotide 744 of IDN1 sequence, consisting on the substitution of a Guanine by a Tymine (G→T), causes the substitution of the aminoacid at position 248 (Glutamine) with Hystidine (Q248H) in the corresponding coded protein and the knock out of the cleavage site of PvuII enzyme. The sequence of the full length cDNA coding for the mutated form of ferroportin at position 248 (Q248H) is reported as IDN7 sequence in the sequences listing annex.

In FIG. 3B is reported the restriction pattern obtained by cleavage with PvuII enzyme of amplified DNA from healthy individuals or carriers of the polymorphism: in healthy subjects having only the wild type sequence, the amplified DNA of 425 bp is cleaved by PvuII restriction enzyme. In hetrozygous carriers subjects, only one allele is cleaved, therefore obtaining three bands: a band of 425 bp (mutated allele) and two bands of 302 and 123 bp (wild type allele).

The invention claimed is:

1. An isolated polynucleotide coding for a ferroportin 1 polypeptide comprising SEQ ID NO:2, wherein the glycine at position 80 of SEQ ID NO:2 is substituted with a serine.

2. The isolated polynucleotide according to claim 1 comprising SEQ ID NO:1, wherein nucleotide 238 of SEQ ID NO:1 is A.

3. The isolated polynucleotide according to claim 1, wherein said isolated polynucleotide is genomic DNA.

4. The isolated polynucleotide according to claim 1, wherein said isolated polynucleotide is mRNA.

5. The isolated polynucleotide according to claim 1, wherein said isolated polynucleotide is cDNA.

6. The isolated polynucleotide coding for a mutated ferroportin 1 according to claim 1, wherein the nucleotide sequence of said isolated polynucleotide is SEQ ID NO:3.

7. The isolated polynucleotide according to claim 1 comprising a label.

8. A recombinant vector comprising the isolated polynucleotide according to claim 1.

9. An isolated cell transfected or transformed with the recombinant vector according to claim 8.

10. A eukaryotic cell, tissue or non-human animal including a transgene, wherein such transgene is at least one isolated polynucleotide according to claim 1.

11. A kit for the non-HFE hereditary Hemochromatosis diagnosis comprising the isolated polynucleotide according to claim 1.

12. A kit for hereditary impaired iron homeostasis diagnosis comprising the isolated polynucleotide according to claim 1.

13. An isolated polynucleotide comprising more than 10 consecutive nucleotides of SEQ ID NO: 3 including nucleotide A at position 238, wherein the isolated polynucleotide further comprises at least one of the oligonucleotide sequences of SEQ ID NO: 13 or the reverse complement of SEQ ID NO:14.

14. A kit for detecting a polymorphism of nucleotide position 238 of SEQ ID NO: 1, wherein the kit consists of at least one of the oligonucleotides of sequence: SEQ ID NO: 13 or 14, optionally in combination with TspR1 restriction enzyme.

* * * * *

SEQUENCE LISTING

```
<160> NUMBER OF SEQ ID NOS: 30

<210> SEQ ID NO 1
<211> LENGTH: 1716
<212> TYPE: DNA
<213> ORGANISM: Homo sapiens
<220> FEATURE:
<221> NAME/KEY: CDS
<222> LOCATION: (1)..(1716)
<223> OTHER INFORMATION: cDNA encoding wild type ferroportin 1.
      Polymorphisms related to the codons:
      238-240 (G80), 520-522 (N174), 742-744 (Q248)

<400> SEQUENCE: 1 atg acc agg gcg gga gat cac aac cgc cag aga gga tgc tgt gga tcc        48
Met Thr Arg Ala Gly Asp His Asn Arg Gln Arg Gly Cys Cys Gly Ser
1               5                   10                  15 ttg gcc gac tac ctg acc tct gca aaa ttc ctt ctc tac ctt ggt cat        96
Leu Ala Asp Tyr Leu Thr Ser Ala Lys Phe Leu Leu Tyr Leu Gly His
                20                  25                  30 tct ctc tct act tgg gga gat cgg atg tgg cac ttt gcg gtg tct gtg       144
Ser Leu Ser Thr Trp Gly Asp Arg Met Trp His Phe Ala Val Ser Val
            35                  40                  45 ttt ctg gta gag ctc tat gga aac agc ctc ctt ttg aca gca gtc tac       192
Phe Leu Val Glu Leu Tyr Gly Asn Ser Leu Leu Leu Thr Ala Val Tyr
        50                  55                  60 ggg ctg gtg gtg gca ggg tct gtt ctg gtc ctg gga gcc atc atc ggt       240
Gly Leu Val Val Ala Gly Ser Val Leu Val Leu Gly Ala Ile Ile Gly
65                  70                  75                  80 gac tgg gtg gac aag aat gct aga ctt aaa gtg gcc cag acc tcg ctg       288
Asp Trp Val Asp Lys Asn Ala Arg Leu Lys Val Ala Gln Thr Ser Leu
                85                  90                  95 gtg gta cag aat gtt tca gtc atc ctg tgt gga atc atc ctg atg atg       336
Val Val Gln Asn Val Ser Val Ile Leu Cys Gly Ile Ile Leu Met Met
            100                 105                 110 gtt ttc tta cat aaa cat gag ctt ctg acc atg tac cat gga tgg gtt       384
Val Phe Leu His Lys His Glu Leu Leu Thr Met Tyr His Gly Trp Val
        115                 120                 125 ctc act tcc tgc tat atc ctg atc atc act att gca aat att gca aat       432
Leu Thr Ser Cys Tyr Ile Leu Ile Ile Thr Ile Ala Asn Ile Ala Asn
130                 135                 140 ttg gcc agt act gct act gca atc aca atc caa agg gat tgg att gtt       480
```

-continued

```
Leu Ala Ser Thr Ala Thr Ala Ile Thr Ile Gln Arg Asp Trp Ile Val
145                 150                 155                 160 gtt gtt gca gga gaa gac aga agc aaa cta gca aat atg aat gcc aca        528
Val Val Ala Gly Glu Asp Arg Ser Lys Leu Ala Asn Met Asn Ala Thr
                165                 170                 175 ata cga agg att gac cag tta acc aac atc tta gcc ccc atg gct gtt        576
Ile Arg Arg Ile Asp Gln Leu Thr Asn Ile Leu Ala Pro Met Ala Val
            180                 185                 190 ggc cag att atg aca ttt ggc tcc cca gtc atc ggc tgt ggc ttt att        624
Gly Gln Ile Met Thr Phe Gly Ser Pro Val Ile Gly Cys Gly Phe Ile
        195                 200                 205 tcg gga tgg aac ttg gta tcc atg tgc gtg gag tac gtc ctg ctc tgg        672
Ser Gly Trp Asn Leu Val Ser Met Cys Val Glu Tyr Val Leu Leu Trp
    210                 215                 220 aag gtt tac cag aaa acc cca gct cta gct gtg aaa gct ggt ctt aaa        720
Lys Val Tyr Gln Lys Thr Pro Ala Leu Ala Val Lys Ala Gly Leu Lys
225                 230                 235                 240 gaa gag gaa act gaa ttg aaa cag ctg aat tta cac aaa gat act gag        768
Glu Glu Glu Thr Glu Leu Lys Gln Leu Asn Leu His Lys Asp Thr Glu
                245                 250                 255 cca aaa ccc ctg gag gga act cat cta atg ggt gtg aaa gac tct aac        816
Pro Lys Pro Leu Glu Gly Thr His Leu Met Gly Val Lys Asp Ser Asn
            260                 265                 270 atc cat gag ctt gaa cat gag caa gag cct act tgt gcc tcc cag atg        864
Ile His Glu Leu Glu His Glu Gln Glu Pro Thr Cys Ala Ser Gln Met
        275                 280                 285 gct gag ccc ttc cgt acc ttc cga gat gga tgg gtc tcc tac tac aac        912
Ala Glu Pro Phe Arg Thr Phe Arg Asp Gly Trp Val Ser Tyr Tyr Asn
    290                 295                 300 cag cct gtg ttt ctg gct ggc atg ggt ctt gct ttc ctt tat atg act        960
Gln Pro Val Phe Leu Ala Gly Met Gly Leu Ala Phe Leu Tyr Met Thr
305                 310                 315                 320 gtc ctg ggc ttt gac tgc atc acc aca ggg tac gcc tac act cag gga       1008
Val Leu Gly Phe Asp Cys Ile Thr Thr Gly Tyr Ala Tyr Thr Gln Gly
                325                 330                 335 ctg agt ggt tcc atc ctc agt att ttg atg gga gca tca gct ata act       1056
Leu Ser Gly Ser Ile Leu Ser Ile Leu Met Gly Ala Ser Ala Ile Thr
            340                 345                 350 gga ata atg gga act gta gct ttt act tgg cta cgt cga aaa tgt ggt       1104
Gly Ile Met Gly Thr Val Ala Phe Thr Trp Leu Arg Arg Lys Cys Gly
        355                 360                 365 ttg gtt cgg aca ggt ctg atc tca gga ttg gca cag ctt tcc tgt ttg       1152
Leu Val Arg Thr Gly Leu Ile Ser Gly Leu Ala Gln Leu Ser Cys Leu
    370                 375                 380 atc ttg tgt gtg atc tct gta ttc atg cct gga agc ccc ctg gac ttg       1200
Ile Leu Cys Val Ile Ser Val Phe Met Pro Gly Ser Pro Leu Asp Leu
385                 390                 395                 400 tcc gtt tct cct ttt gaa gat atc cga tca agg ttc att caa gga gag       1248
Ser Val Ser Pro Phe Glu Asp Ile Arg Ser Arg Phe Ile Gln Gly Glu
                405                 410                 415 tca att aca cct acc aag ata cct gaa att aca act gaa ata tac atg       1296
Ser Ile Thr Pro Thr Lys Ile Pro Glu Ile Thr Thr Glu Ile Tyr Met
            420                 425                 430 tct aat ggg tct aat tct gct aat att gtc ccg gag aca agt cct gaa       1344
Ser Asn Gly Ser Asn Ser Ala Asn Ile Val Pro Glu Thr Ser Pro Glu
        435                 440                 445 tct gtg ccc ata atc tct gtc agt ctg ctg ttt gca ggc gtc att gct       1392
Ser Val Pro Ile Ile Ser Val Ser Leu Leu Phe Ala Gly Val Ile Ala
    450                 455                 460
```

```
gct aga atc ggt ctt tgg tcc ttt gat tta act gtg aca cag ttg ctg    1440
Ala Arg Ile Gly Leu Trp Ser Phe Asp Leu Thr Val Thr Gln Leu Leu
465                 470                 475                 480 caa gaa aat gta att gaa tct gaa aga ggc att ata aat ggt gta cag    1488
Gln Glu Asn Val Ile Glu Ser Glu Arg Gly Ile Ile Asn Gly Val Gln
                485                 490                 495 aac tcc atg aac tat ctt ctt gat ctt ctg cat ttc atc atg gtc atc    1536
Asn Ser Met Asn Tyr Leu Leu Asp Leu Leu His Phe Ile Met Val Ile
            500                 505                 510 ctg gct cca aat cct gaa gct ttt ggc ttg ctc gta ttg att tca gtc    1584
Leu Ala Pro Asn Pro Glu Ala Phe Gly Leu Leu Val Leu Ile Ser Val
        515                 520                 525 tcc ttt gtg gca atg ggc cac att atg tat ttc cga ttt gcc caa aat    1632
Ser Phe Val Ala Met Gly His Ile Met Tyr Phe Arg Phe Ala Gln Asn
    530                 535                 540 act ctg gga aac aag ctc ttt gct tgc ggt cct gat gca aaa gaa gtt    1680
Thr Leu Gly Asn Lys Leu Phe Ala Cys Gly Pro Asp Ala Lys Glu Val
545                 550                 555                 560 agg aag gaa aat caa gca aat aca tct gtt gtt tga                    1716
Arg Lys Glu Asn Gln Ala Asn Thr Ser Val Val
                565                 570

<210> SEQ ID NO 2
<211> LENGTH: 571
<212> TYPE: PRT
<213> ORGANISM: Homo sapiens

<400> SEQUENCE: 2

Met Thr Arg Ala Gly Asp His Asn Arg Gln Arg Gly Cys Cys Gly Ser
1               5                   10                  15

Leu Ala Asp Tyr Leu Thr Ser Ala Lys Phe Leu Leu Tyr Leu Gly His
                20                  25                  30

Ser Leu Ser Thr Trp Gly Asp Arg Met Trp His Phe Ala Val Ser Val
            35                  40                  45

Phe Leu Val Glu Leu Tyr Gly Asn Ser Leu Leu Leu Thr Ala Val Tyr
        50                  55                  60

Gly Leu Val Val Ala Gly Ser Val Leu Val Leu Gly Ala Ile Ile Gly
65                  70                  75                  80

Asp Trp Val Asp Lys Asn Ala Arg Leu Lys Val Ala Gln Thr Ser Leu
                85                  90                  95

Val Val Gln Asn Val Ser Val Ile Leu Cys Gly Ile Ile Leu Met Met
                100                 105                 110

Val Phe Leu His Lys His Glu Leu Leu Thr Met Tyr His Gly Trp Val
        115                 120                 125

Leu Thr Ser Cys Tyr Ile Leu Ile Ile Thr Ile Ala Asn Ile Ala Asn
    130                 135                 140

Leu Ala Ser Thr Ala Thr Ala Ile Thr Ile Gln Arg Asp Trp Ile Val
145                 150                 155                 160

Val Val Ala Gly Glu Asp Arg Ser Lys Leu Ala Asn Met Asn Ala Thr
                165                 170                 175

Ile Arg Arg Ile Asp Gln Leu Thr Asn Ile Leu Ala Pro Met Ala Val
            180                 185                 190

Gly Gln Ile Met Thr Phe Gly Ser Pro Val Ile Gly Cys Gly Phe Ile
        195                 200                 205

Ser Gly Trp Asn Leu Val Ser Met Cys Val Glu Tyr Val Leu Leu Trp
    210                 215                 220

Lys Val Tyr Gln Lys Thr Pro Ala Leu Ala Val Lys Ala Gly Leu Lys
```

-continued

```
            225                 230                 235                 240
Glu Glu Glu Thr Glu Leu Lys Gln Leu Asn Leu His Lys Asp Thr Glu
                245                 250                 255

Pro Lys Pro Leu Glu Gly Thr His Leu Met Gly Val Lys Asp Ser Asn
            260                 265                 270

Ile His Glu Leu Glu His Glu Gln Glu Pro Thr Cys Ala Ser Gln Met
            275                 280                 285

Ala Glu Pro Phe Arg Thr Phe Arg Asp Gly Trp Val Ser Tyr Tyr Asn
        290                 295                 300

Gln Pro Val Phe Leu Ala Gly Met Gly Leu Ala Phe Leu Tyr Met Thr
305                 310                 315                 320

Val Leu Gly Phe Asp Cys Ile Thr Thr Gly Tyr Ala Tyr Thr Gln Gly
                325                 330                 335

Leu Ser Gly Ser Ile Leu Ser Ile Leu Met Gly Ala Ser Ala Ile Thr
                340                 345                 350

Gly Ile Met Gly Thr Val Ala Phe Thr Trp Leu Arg Arg Lys Cys Gly
                355                 360                 365

Leu Val Arg Thr Gly Leu Ile Ser Gly Leu Ala Gln Leu Ser Cys Leu
        370                 375                 380

Ile Leu Cys Val Ile Ser Val Phe Met Pro Gly Ser Pro Leu Asp Leu
385                 390                 395                 400

Ser Val Ser Pro Phe Glu Asp Ile Arg Ser Arg Phe Ile Gln Gly Glu
                405                 410                 415

Ser Ile Thr Pro Thr Lys Ile Pro Glu Ile Thr Thr Glu Ile Tyr Met
                420                 425                 430

Ser Asn Gly Ser Asn Ser Ala Asn Ile Val Pro Glu Thr Ser Pro Glu
                435                 440                 445

Ser Val Pro Ile Ile Ser Val Ser Leu Leu Phe Ala Gly Val Ile Ala
            450                 455                 460

Ala Arg Ile Gly Leu Trp Ser Phe Asp Leu Thr Val Thr Gln Leu Leu
465                 470                 475                 480

Gln Glu Asn Val Ile Glu Ser Glu Arg Gly Ile Ile Asn Gly Val Gln
                485                 490                 495

Asn Ser Met Asn Tyr Leu Leu Asp Leu Leu His Phe Ile Met Val Ile
                500                 505                 510

Leu Ala Pro Asn Pro Glu Ala Phe Gly Leu Leu Val Leu Ile Ser Val
            515                 520                 525

Ser Phe Val Ala Met Gly His Ile Met Tyr Phe Arg Phe Ala Gln Asn
        530                 535                 540

Thr Leu Gly Asn Lys Leu Phe Ala Cys Gly Pro Asp Ala Lys Glu Val
545                 550                 555                 560

Arg Lys Glu Asn Gln Ala Asn Thr Ser Val Val
                565                 570
```

<210> SEQ ID NO 3
<211> LENGTH: 1716
<212> TYPE: DNA
<213> ORGANISM: Homo sapiens
<220> FEATURE:
<221> NAME/KEY: CDS
<222> LOCATION: (1)..(1716)
<223> OTHER INFORMATION: cDNA encoding a ferroportin 1 mutated in
      position (G80).

<400> SEQUENCE: 3 atg acc agg gcg gga gat cac aac cgc cag aga gga tgc tgt gga tcc        48

```
Met Thr Arg Ala Gly Asp His Asn Arg Gln Arg Gly Cys Cys Gly Ser
1               5                   10                  15 ttg gcc gac tac ctg acc tct gca aaa ttc ctt ctc tac ctt ggt cat        96
Leu Ala Asp Tyr Leu Thr Ser Ala Lys Phe Leu Leu Tyr Leu Gly His
            20                  25                  30 tct ctc tct act tgg gga gat cgg atg tgg cac ttt gcg gtg tct gtg       144
Ser Leu Ser Thr Trp Gly Asp Arg Met Trp His Phe Ala Val Ser Val
            35                  40                  45 ttt ctg gta gag ctc tat gga aac agc ctc ctt ttg aca gca gtc tac       192
Phe Leu Val Glu Leu Tyr Gly Asn Ser Leu Leu Leu Thr Ala Val Tyr
50                  55                  60 ggg ctg gtg gtg gca ggg tct gtt ctg gtc ctg gga gcc atc atc agt       240
Gly Leu Val Val Ala Gly Ser Val Leu Val Leu Gly Ala Ile Ile Ser
65                  70                  75                  80 gac tgg gtg gac aag aat gct aga ctt aaa gtg gcc cag acc tcg ctg       288
Asp Trp Val Asp Lys Asn Ala Arg Leu Lys Val Ala Gln Thr Ser Leu
                85                  90                  95 gtg gta cag aat gtt tca gtc atc ctg tgt gga atc atc ctg atg atg       336
Val Val Gln Asn Val Ser Val Ile Leu Cys Gly Ile Ile Leu Met Met
            100                 105                 110 gtt ttc tta cat aaa cat gag ctt ctg acc atg tac cat gga tgg gtt       384
Val Phe Leu His Lys His Glu Leu Leu Thr Met Tyr His Gly Trp Val
            115                 120                 125 ctc act tcc tgc tat atc ctg atc atc act att gca aat att gca aat       432
Leu Thr Ser Cys Tyr Ile Leu Ile Ile Thr Ile Ala Asn Ile Ala Asn
130                 135                 140 ttg gcc agt act gct act gca atc aca atc caa agg gat tgg att gtt       480
Leu Ala Ser Thr Ala Thr Ala Ile Thr Ile Gln Arg Asp Trp Ile Val
145                 150                 155                 160 gtt gtt gca gga gaa gac aga agc aaa cta gca aat atg aat gcc aca       528
Val Val Ala Gly Glu Asp Arg Ser Lys Leu Ala Asn Met Asn Ala Thr
                165                 170                 175 ata cga agg att gac cag tta acc aac atc tta gcc ccc atg gct gtt       576
Ile Arg Arg Ile Asp Gln Leu Thr Asn Ile Leu Ala Pro Met Ala Val
            180                 185                 190 ggc cag att atg aca ttt ggc tcc cca gtc atc ggc tgt ggc ttt att       624
Gly Gln Ile Met Thr Phe Gly Ser Pro Val Ile Gly Cys Gly Phe Ile
            195                 200                 205 tcg gga tgg aac ttg gta tcc atg tgc gtg gag tac gtc ctg ctc tgg       672
Ser Gly Trp Asn Leu Val Ser Met Cys Val Glu Tyr Val Leu Leu Trp
210                 215                 220 aag gtt tac cag aaa acc cca gct cta gct gtg aaa gct ggt ctt aaa       720
Lys Val Tyr Gln Lys Thr Pro Ala Leu Ala Val Lys Ala Gly Leu Lys
225                 230                 235                 240 gaa gag gaa act gaa ttg aaa cag ctg aat tta cac aaa gat act gag       768
Glu Glu Glu Thr Glu Leu Lys Gln Leu Asn Leu His Lys Asp Thr Glu
                245                 250                 255 cca aaa ccc ctg gag gga act cat cta atg ggt gtg aaa gac tct aac       816
Pro Lys Pro Leu Glu Gly Thr His Leu Met Gly Val Lys Asp Ser Asn
            260                 265                 270 atc cat gag ctt gaa cat gag caa gag cct act tgt gcc tcc cag atg       864
Ile His Glu Leu Glu His Glu Gln Glu Pro Thr Cys Ala Ser Gln Met
            275                 280                 285 gct gag ccc ttc cgt acc ttc cga gat gga tgg gtc tcc tac tac aac       912
Ala Glu Pro Phe Arg Thr Phe Arg Asp Gly Trp Val Ser Tyr Tyr Asn
            290                 295                 300 cag cct gtg ttt ctg gct ggc atg ggc ttg gct ttc ctt tat atg act       960
Gln Pro Val Phe Leu Ala Gly Met Gly Leu Ala Phe Leu Tyr Met Thr
305                 310                 315                 320
```

```
gtc ctg ggc ttt gac tgc atc acc aca ggg tac gcc tac act cag gga    1008
Val Leu Gly Phe Asp Cys Ile Thr Thr Gly Tyr Ala Tyr Thr Gln Gly
            325                 330                 335 ctg agt ggt tcc atc ctc agt att ttg atg gga gca tca gct ata act    1056
Leu Ser Gly Ser Ile Leu Ser Ile Leu Met Gly Ala Ser Ala Ile Thr
        340                 345                 350 gga ata atg gga act gta gct ttt act tgg cta cgt cga aaa tgt ggt    1104
Gly Ile Met Gly Thr Val Ala Phe Thr Trp Leu Arg Arg Lys Cys Gly
    355                 360                 365 ttg gtt cgg aca ggt ctg atc tca gga ttg gca cag ctt tcc tgt ttg    1152
Leu Val Arg Thr Gly Leu Ile Ser Gly Leu Ala Gln Leu Ser Cys Leu
370                 375                 380 atc ttg tgt gtg atc tct gta ttc atg cct gga agc ccc ctg gac ttg    1200
Ile Leu Cys Val Ile Ser Val Phe Met Pro Gly Ser Pro Leu Asp Leu
385                 390                 395                 400 tcc gtt tct cct ttt gaa gat atc cga tca agg ttc att caa gga gag    1248
Ser Val Ser Pro Phe Glu Asp Ile Arg Ser Arg Phe Ile Gln Gly Glu
            405                 410                 415 tca att aca cct acc aag ata cct gaa att aca act gaa ata tac atg    1296
Ser Ile Thr Pro Thr Lys Ile Pro Glu Ile Thr Thr Glu Ile Tyr Met
        420                 425                 430 tct aat ggg tct aat tct gct aat att gtc ccg gag aca agt cct gaa    1344
Ser Asn Gly Ser Asn Ser Ala Asn Ile Val Pro Glu Thr Ser Pro Glu
    435                 440                 445 tct gtg ccc ata atc tct gtc agt ctg ctg ttt gca ggc gtc att gct    1392
Ser Val Pro Ile Ile Ser Val Ser Leu Leu Phe Ala Gly Val Ile Ala
450                 455                 460 gct aga atc ggt ctt tgg tcc ttt gat tta act gtg aca cag ttg ctg    1440
Ala Arg Ile Gly Leu Trp Ser Phe Asp Leu Thr Val Thr Gln Leu Leu
465                 470                 475                 480 caa gaa aat gta att gaa tct gaa aga ggc att ata aat ggt gta cag    1488
Gln Glu Asn Val Ile Glu Ser Glu Arg Gly Ile Ile Asn Gly Val Gln
            485                 490                 495 aac tcc atg aac tat ctt ctt gat ctt ctg cat ttc atc atg gtc atc    1536
Asn Ser Met Asn Tyr Leu Leu Asp Leu Leu His Phe Ile Met Val Ile
        500                 505                 510 ctg gct cca aat cct gaa gct ttt ggc ttg ctc gta ttg att tca gtc    1584
Leu Ala Pro Asn Pro Glu Ala Phe Gly Leu Leu Val Leu Ile Ser Val
    515                 520                 525 tcc ttt gtg gca atg ggc cac att atg tat ttc cga ttt gcc caa aat    1632
Ser Phe Val Ala Met Gly His Ile Met Tyr Phe Arg Phe Ala Gln Asn
530                 535                 540 act ctg gga aac aag ctc ttt gct tgc ggt cct gat gca aaa gaa gtt    1680
Thr Leu Gly Asn Lys Leu Phe Ala Cys Gly Pro Asp Ala Lys Glu Val
545                 550                 555                 560 agg aag gaa aat caa gca aat aca tct gtt gtt tga                    1716
Arg Lys Glu Asn Gln Ala Asn Thr Ser Val Val
            565                 570

<210> SEQ ID NO 4
<211> LENGTH: 571
<212> TYPE: PRT
<213> ORGANISM: Homo sapiens

<400> SEQUENCE: 4

Met Thr Arg Ala Gly Asp His Asn Arg Gln Arg Gly Cys Cys Gly Ser
1               5                   10                  15

Leu Ala Asp Tyr Leu Thr Ser Ala Lys Phe Leu Leu Tyr Leu Gly His
            20                  25                  30

Ser Leu Ser Thr Trp Gly Asp Arg Met Trp His Phe Ala Val Ser Val
```

```
                35                  40                  45
Phe Leu Val Glu Leu Tyr Gly Asn Ser Leu Leu Thr Ala Val Tyr
 50                  55                  60

Gly Leu Val Val Ala Gly Ser Val Leu Val Leu Gly Ala Ile Ile Ser
 65                  70                  75                  80

Asp Trp Val Asp Lys Asn Ala Arg Leu Lys Val Ala Gln Thr Ser Leu
                 85                  90                  95

Val Val Gln Asn Val Ser Val Ile Leu Cys Gly Ile Ile Leu Met Met
                100                 105                 110

Val Phe Leu His Lys His Glu Leu Leu Thr Met Tyr His Gly Trp Val
                115                 120                 125

Leu Thr Ser Cys Tyr Ile Leu Ile Ile Thr Ile Ala Asn Ile Ala Asn
130                 135                 140

Leu Ala Ser Thr Ala Thr Ala Ile Thr Ile Gln Arg Asp Trp Ile Val
145                 150                 155                 160

Val Val Ala Gly Glu Asp Arg Ser Lys Leu Ala Asn Met Asn Ala Thr
                165                 170                 175

Ile Arg Arg Ile Asp Gln Leu Thr Asn Ile Leu Ala Pro Met Ala Val
                180                 185                 190

Gly Gln Ile Met Thr Phe Gly Ser Pro Val Ile Gly Cys Gly Phe Ile
                195                 200                 205

Ser Gly Trp Asn Leu Val Ser Met Cys Val Glu Tyr Val Leu Leu Trp
210                 215                 220

Lys Val Tyr Gln Lys Thr Pro Ala Leu Ala Val Lys Ala Gly Leu Lys
225                 230                 235                 240

Glu Glu Glu Thr Glu Leu Lys Gln Leu Asn Leu His Lys Asp Thr Glu
                245                 250                 255

Pro Lys Pro Leu Glu Gly Thr His Leu Met Gly Val Lys Asp Ser Asn
                260                 265                 270

Ile His Glu Leu Glu His Glu Gln Glu Pro Thr Cys Ala Ser Gln Met
                275                 280                 285

Ala Glu Pro Phe Arg Thr Phe Arg Asp Gly Trp Val Ser Tyr Tyr Asn
290                 295                 300

Gln Pro Val Phe Leu Ala Gly Met Gly Leu Ala Phe Leu Tyr Met Thr
305                 310                 315                 320

Val Leu Gly Phe Asp Cys Ile Thr Thr Gly Tyr Ala Tyr Thr Gln Gly
                325                 330                 335

Leu Ser Gly Ser Ile Leu Ser Ile Leu Met Gly Ala Ser Ala Ile Thr
                340                 345                 350

Gly Ile Met Gly Thr Val Ala Phe Thr Trp Leu Arg Arg Lys Cys Gly
                355                 360                 365

Leu Val Arg Thr Gly Leu Ile Ser Gly Leu Ala Gln Leu Ser Cys Leu
370                 375                 380

Ile Leu Cys Val Ile Ser Val Phe Met Pro Gly Ser Pro Leu Asp Leu
385                 390                 395                 400

Ser Val Ser Pro Phe Glu Asp Ile Arg Ser Arg Phe Ile Gln Gly Glu
                405                 410                 415

Ser Ile Thr Pro Thr Lys Ile Pro Glu Ile Thr Thr Glu Ile Tyr Met
                420                 425                 430

Ser Asn Gly Ser Asn Ser Ala Asn Ile Val Pro Glu Thr Ser Pro Glu
                435                 440                 445

Ser Val Pro Ile Ile Ser Val Ser Leu Leu Phe Ala Gly Val Ile Ala
450                 455                 460
```

-continued

```
Ala Arg Ile Gly Leu Trp Ser Phe Asp Leu Thr Val Thr Gln Leu Leu
465                 470                 475                 480

Gln Glu Asn Val Ile Glu Ser Glu Arg Gly Ile Ile Asn Gly Val Gln
            485                 490                 495

Asn Ser Met Asn Tyr Leu Leu Asp Leu Leu His Phe Ile Met Val Ile
            500                 505                 510

Leu Ala Pro Asn Pro Glu Ala Phe Gly Leu Leu Val Leu Ile Ser Val
            515                 520                 525

Ser Phe Val Ala Met Gly His Ile Met Tyr Phe Arg Phe Ala Gln Asn
            530                 535                 540

Thr Leu Gly Asn Lys Leu Phe Ala Cys Gly Pro Asp Ala Lys Glu Val
545                 550                 555                 560

Arg Lys Glu Asn Gln Ala Asn Thr Ser Val Val
            565                 570
```

```
<210> SEQ ID NO 5
<211> LENGTH: 1716
<212> TYPE: DNA
<213> ORGANISM: Homo sapiens
<220> FEATURE:
<221> NAME/KEY: CDS
<222> LOCATION: (1)..(1716)
<223> OTHER INFORMATION: cDNAencoding a ferroportin 1 mutated in
      position 174 (N174)

<400> SEQUENCE: 5
```

```
atg acc agg gcg gga gat cac aac cgc cag aga gga tgc tgt gga tcc      48
Met Thr Arg Ala Gly Asp His Asn Arg Gln Arg Gly Cys Cys Gly Ser
1               5                   10                  15 ttg gcc gac tac ctg acc tct gca aaa ttc ctt ctc tac ctt ggt cat      96
Leu Ala Asp Tyr Leu Thr Ser Ala Lys Phe Leu Leu Tyr Leu Gly His
                20                  25                  30 tct ctc tct act tgg gga gat cgg atg tgg cac ttt gcg gtg tct gtg     144
Ser Leu Ser Thr Trp Gly Asp Arg Met Trp His Phe Ala Val Ser Val
            35                  40                  45 ttt ctg gta gag ctc tat gga aac agc ctc ctt ttg aca gca gtc tac     192
Phe Leu Val Glu Leu Tyr Gly Asn Ser Leu Leu Leu Thr Ala Val Tyr
        50                  55                  60 ggg ctg gtg gtg gca ggg tct gtt ctg gtc ctg gga gcc atc atc ggt     240
Gly Leu Val Val Ala Gly Ser Val Leu Val Leu Gly Ala Ile Ile Gly
65                  70                  75                  80 gac tgg gtg gac aag aat gct aga ctt aaa gtg gcc cag acc tcg ctg     288
Asp Trp Val Asp Lys Asn Ala Arg Leu Lys Val Ala Gln Thr Ser Leu
                85                  90                  95 gtg gta cag aat gtt tca gtc atc ctg tgt gga atc atc ctg atg atg     336
Val Val Gln Asn Val Ser Val Ile Leu Cys Gly Ile Ile Leu Met Met
            100                 105                 110 gtt ttc tta cat aaa cat gag ctt ctg acc atg tac cat gga tgg gtt     384
Val Phe Leu His Lys His Glu Leu Leu Thr Met Tyr His Gly Trp Val
        115                 120                 125 ctc act tcc tgc tat atc ctg atc atc act att gca aat att gca aat     432
Leu Thr Ser Cys Tyr Ile Leu Ile Ile Thr Ile Ala Asn Ile Ala Asn
130                 135                 140 ttg gcc agt act gct act gca atc aca atc caa agg gat tgg att gtt     480
Leu Ala Ser Thr Ala Thr Ala Ile Thr Ile Gln Arg Asp Trp Ile Val
145                 150                 155                 160 gtt gtt gca gga gaa gac aga agc aaa cta gca aat atg att gcc aca     528
Val Val Ala Gly Glu Asp Arg Ser Lys Leu Ala Asn Met Ile Ala Thr
                165                 170                 175
```

-continued

| | | |
|---|---|---|
| ata cga agg att gac cag tta acc aac atc tta gcc ccc atg gct gtt<br>Ile Arg Arg Ile Asp Gln Leu Thr Asn Ile Leu Ala Pro Met Ala Val<br>180 185 190 | 576 | |
| ggc cag att atg aca ttt ggc tcc cca gtc atc ggc tgt ggc ttt att<br>Gly Gln Ile Met Thr Phe Gly Ser Pro Val Ile Gly Cys Gly Phe Ile<br>195 200 205 | 624 | |
| tcg gga tgg aac ttg gta tcc atg tgc gtg gag tac gtc ctg ctc tgg<br>Ser Gly Trp Asn Leu Val Ser Met Cys Val Glu Tyr Val Leu Leu Trp<br>210 215 220 | 672 | |
| aag gtt tac cag aaa acc cca gct cta gct gtg aaa gct ggt ctt aaa<br>Lys Val Tyr Gln Lys Thr Pro Ala Leu Ala Val Lys Ala Gly Leu Lys<br>225 230 235 240 | 720 | |
| gaa gag gaa act gaa ttg aaa cag ctg aat tta cac aaa gat act gag<br>Glu Glu Glu Thr Glu Leu Lys Gln Leu Asn Leu His Lys Asp Thr Glu<br>245 250 255 | 768 | |
| cca aaa ccc ctg gag gga act cat cta atg ggt gtg aaa gac tct aac<br>Pro Lys Pro Leu Glu Gly Thr His Leu Met Gly Val Lys Asp Ser Asn<br>260 265 270 | 816 | |
| atc cat gag ctt gaa cat gag caa gag cct act tgt gcc tcc cag atg<br>Ile His Glu Leu Glu His Glu Gln Glu Pro Thr Cys Ala Ser Gln Met<br>275 280 285 | 864 | |
| gct gag ccc ttc cgt acc ttc cga gat gga tgg gtc tcc tac tac aac<br>Ala Glu Pro Phe Arg Thr Phe Arg Asp Gly Trp Val Ser Tyr Tyr Asn<br>290 295 300 | 912 | |
| cag cct gtg ttt ctg gct ggc atg ggt ctt gct ttc ctt tat atg act<br>Gln Pro Val Phe Leu Ala Gly Met Gly Leu Ala Phe Leu Tyr Met Thr<br>305 310 315 320 | 960 | |
| gtc ctg ggc ttt gac tgc atc acc aca ggg tac gcc tac act cag gga<br>Val Leu Gly Phe Asp Cys Ile Thr Thr Gly Tyr Ala Tyr Thr Gln Gly<br>325 330 335 | 1008 | |
| ctg agt ggt tcc atc ctc agt att ttg atg gga gca tca gct ata act<br>Leu Ser Gly Ser Ile Leu Ser Ile Leu Met Gly Ala Ser Ala Ile Thr<br>340 345 350 | 1056 | |
| gga ata atg gga act gta gct ttt act tgg cta cgt cga aaa tgt ggt<br>Gly Ile Met Gly Thr Val Ala Phe Thr Trp Leu Arg Arg Lys Cys Gly<br>355 360 365 | 1104 | |
| ttg gtt cgg aca ggt ctg atc tca gga ttg gca cag ctt tcc tgt ttg<br>Leu Val Arg Thr Gly Leu Ile Ser Gly Leu Ala Gln Leu Ser Cys Leu<br>370 375 380 | 1152 | |
| atc ttg tgt gtg atc tct gta ttc atg cct gga agc ccc ctg gac ttg<br>Ile Leu Cys Val Ile Ser Val Phe Met Pro Gly Ser Pro Leu Asp Leu<br>385 390 395 400 | 1200 | |
| tcc gtt tct cct ttt gaa gat atc cga tca agg ttc att caa gga gag<br>Ser Val Ser Pro Phe Glu Asp Ile Arg Ser Arg Phe Ile Gln Gly Glu<br>405 410 415 | 1248 | |
| tca att aca cct acc aag ata cct gaa att aca act gaa ata tac atg<br>Ser Ile Thr Pro Thr Lys Ile Pro Glu Ile Thr Thr Glu Ile Tyr Met<br>420 425 430 | 1296 | |
| tct aat ggg tct aat tct gct aat att gtc ccg gag aca agt cct gaa<br>Ser Asn Gly Ser Asn Ser Ala Asn Ile Val Pro Glu Thr Ser Pro Glu<br>435 440 445 | 1344 | |
| tct gtg ccc ata atc tct gtc agt ctg ctg ttt gca ggc gtc att gct<br>Ser Val Pro Ile Ile Ser Val Ser Leu Leu Phe Ala Gly Val Ile Ala<br>450 455 460 | 1392 | |
| gct aga atc ggt ctt tgg tcc ttt gat tta act gtg aca cag ttg ctg<br>Ala Arg Ile Gly Leu Trp Ser Phe Asp Leu Thr Val Thr Gln Leu Leu<br>465 470 475 480 | 1440 | |
| caa gaa aat gta att gaa tct gaa aga ggc att ata aat ggt gta cag<br>Gln Glu Asn Val Ile Glu Ser Glu Arg Gly Ile Ile Asn Gly Val Gln<br>485 490 495 | 1488 | |

-continued

```
aac tcc atg aac tat ctt ctt gat ctt ctg cat ttc atc atg gtc atc      1536
Asn Ser Met Asn Tyr Leu Leu Asp Leu Leu His Phe Ile Met Val Ile
            500                 505                 510 ctg gct cca aat cct gaa gct ttt ggc ttg ctc gta ttg att tca gtc      1584
Leu Ala Pro Asn Pro Glu Ala Phe Gly Leu Leu Val Leu Ile Ser Val
        515                 520                 525 tcc ttt gtg gca atg ggc cac att atg tat ttc cga ttt gcc caa aat      1632
Ser Phe Val Ala Met Gly His Ile Met Tyr Phe Arg Phe Ala Gln Asn
    530                 535                 540 act ctg gga aac aag ctc ttt gct tgc ggt cct gat gca aaa gaa gtt      1680
Thr Leu Gly Asn Lys Leu Phe Ala Cys Gly Pro Asp Ala Lys Glu Val
545                 550                 555                 560 agg aag gaa aat caa gca aat aca tct gtt gtt tga                      1716
Arg Lys Glu Asn Gln Ala Asn Thr Ser Val Val
                565                 570

<210> SEQ ID NO 6
<211> LENGTH: 571
<212> TYPE: PRT
<213> ORGANISM: Homo sapiens

<400> SEQUENCE: 6

Met Thr Arg Ala Gly Asp His Asn Arg Gln Arg Gly Cys Cys Gly Ser
1               5                   10                  15

Leu Ala Asp Tyr Leu Thr Ser Ala Lys Phe Leu Leu Tyr Leu Gly His
            20                  25                  30

Ser Leu Ser Thr Trp Gly Asp Arg Met Trp His Phe Ala Val Ser Val
        35                  40                  45

Phe Leu Val Glu Leu Tyr Gly Asn Ser Leu Leu Leu Thr Ala Val Tyr
    50                  55                  60

Gly Leu Val Val Ala Gly Ser Val Leu Val Leu Gly Ala Ile Ile Gly
65                  70                  75                  80

Asp Trp Val Asp Lys Asn Ala Arg Leu Lys Val Ala Gln Thr Ser Leu
                85                  90                  95

Val Val Gln Asn Val Ser Val Ile Leu Cys Gly Ile Ile Leu Met Met
            100                 105                 110

Val Phe Leu His Lys His Glu Leu Leu Thr Met Tyr His Gly Trp Val
        115                 120                 125

Leu Thr Ser Cys Tyr Ile Leu Ile Ile Thr Ile Ala Asn Ile Ala Asn
    130                 135                 140

Leu Ala Ser Thr Ala Thr Ala Ile Thr Ile Gln Arg Asp Trp Ile Val
145                 150                 155                 160

Val Val Ala Gly Glu Asp Arg Ser Lys Leu Ala Asn Met Ile Ala Thr
                165                 170                 175

Ile Arg Arg Ile Asp Gln Leu Thr Asn Ile Leu Ala Pro Met Ala Val
            180                 185                 190

Gly Gln Ile Met Thr Phe Gly Ser Pro Val Ile Gly Cys Gly Phe Ile
        195                 200                 205

Ser Gly Trp Asn Leu Val Ser Met Cys Val Glu Tyr Val Leu Leu Trp
    210                 215                 220

Lys Val Tyr Gln Lys Thr Pro Ala Leu Ala Val Lys Ala Gly Leu Lys
225                 230                 235                 240

Glu Glu Glu Thr Glu Leu Lys Gln Leu Asn Leu His Lys Asp Thr Glu
                245                 250                 255

Pro Lys Pro Leu Glu Gly Thr His Leu Met Gly Val Lys Asp Ser Asn
            260                 265                 270
```

```
Ile His Glu Leu Glu His Glu Gln Glu Pro Thr Cys Ala Ser Gln Met
        275                 280                 285

Ala Glu Pro Phe Arg Thr Phe Arg Asp Gly Trp Val Ser Tyr Tyr Asn
290                 295                 300

Gln Pro Val Phe Leu Ala Gly Met Gly Leu Ala Phe Leu Tyr Met Thr
305                 310                 315                 320

Val Leu Gly Phe Asp Cys Ile Thr Thr Gly Tyr Ala Tyr Thr Gln Gly
                325                 330                 335

Leu Ser Gly Ser Ile Leu Ser Ile Leu Met Gly Ala Ser Ala Ile Thr
                340                 345                 350

Gly Ile Met Gly Thr Val Ala Phe Thr Trp Leu Arg Arg Lys Cys Gly
        355                 360                 365

Leu Val Arg Thr Gly Leu Ile Ser Gly Leu Ala Gln Leu Ser Cys Leu
    370                 375                 380

Ile Leu Cys Val Ile Ser Val Phe Met Pro Gly Ser Pro Leu Asp Leu
385                 390                 395                 400

Ser Val Ser Pro Phe Glu Asp Ile Arg Ser Arg Phe Ile Gln Gly Glu
                405                 410                 415

Ser Ile Thr Pro Thr Lys Ile Pro Glu Ile Thr Glu Ile Tyr Met
                420                 425                 430

Ser Asn Gly Ser Asn Ser Ala Asn Ile Val Pro Glu Thr Ser Pro Glu
        435                 440                 445

Ser Val Pro Ile Ile Ser Val Ser Leu Leu Phe Ala Gly Val Ile Ala
    450                 455                 460

Ala Arg Ile Gly Leu Trp Ser Phe Asp Leu Thr Val Thr Gln Leu Leu
465                 470                 475                 480

Gln Glu Asn Val Ile Glu Ser Glu Arg Gly Ile Ile Asn Gly Val Gln
                485                 490                 495

Asn Ser Met Asn Tyr Leu Leu Asp Leu Leu His Phe Ile Met Val Ile
        500                 505                 510

Leu Ala Pro Asn Pro Glu Ala Phe Gly Leu Leu Val Leu Ile Ser Val
    515                 520                 525

Ser Phe Val Ala Met Gly His Ile Met Tyr Phe Arg Phe Ala Gln Asn
530                 535                 540

Thr Leu Gly Asn Lys Leu Phe Ala Cys Gly Pro Asp Ala Lys Glu Val
545                 550                 555                 560

Arg Lys Glu Asn Gln Ala Asn Thr Ser Val Val
                565                 570

<210> SEQ ID NO 7
<211> LENGTH: 1716
<212> TYPE: DNA
<213> ORGANISM: Homo sapiens
<220> FEATURE:
<221> NAME/KEY: CDS
<222> LOCATION: (1)..(1716)
<223> OTHER INFORMATION: cDNA encoding a ferroportina 1 mutated in
      position 248 (Q248).

<400> SEQUENCE: 7 atg acc agg gcg gga gat cac aac cgc cag aga gga tgc tgt gga tcc      48
Met Thr Arg Ala Gly Asp His Asn Arg Gln Arg Gly Cys Cys Gly Ser
1               5                   10                  15 ttg gcc gac tac ctg acc tct gca aaa ttc ctt ctc tac ctt ggt cat      96
Leu Ala Asp Tyr Leu Thr Ser Ala Lys Phe Leu Leu Tyr Leu Gly His
            20                  25                  30
```

```
tct ctc tct act tgg gga gat cgg atg tgg cac ttt gcg gtg tct gtg      144
Ser Leu Ser Thr Trp Gly Asp Arg Met Trp His Phe Ala Val Ser Val
        35              40              45 ttt ctg gta gag ctc tat gga aac agc ctc ctt ttg aca gca gtc tac      192
Phe Leu Val Glu Leu Tyr Gly Asn Ser Leu Leu Leu Thr Ala Val Tyr
    50              55              60 ggg ctg gtg gtg gca ggg tct gtt ctg gtc ctg gga gcc atc atc ggt      240
Gly Leu Val Val Ala Gly Ser Val Leu Val Leu Gly Ala Ile Ile Gly
65              70              75              80 gac tgg gtg gac aag aat gct aga ctt aaa gtg gcc cag acc tcg ctg      288
Asp Trp Val Asp Lys Asn Ala Arg Leu Lys Val Ala Gln Thr Ser Leu
                85              90              95 gtg gta cag aat gtt tca gtc atc ctg tgt gga atc atc ctg atg atg      336
Val Val Gln Asn Val Ser Val Ile Leu Cys Gly Ile Ile Leu Met Met
            100             105             110 gtt ttc tta cat aaa cat gag ctt ctg acc atg tac cat gga tgg gtt      384
Val Phe Leu His Lys His Glu Leu Leu Thr Met Tyr His Gly Trp Val
        115             120             125 ctc act tcc tgc tat atc ctg atc atc act att gca aat att gca aat      432
Leu Thr Ser Cys Tyr Ile Leu Ile Ile Thr Ile Ala Asn Ile Ala Asn
    130             135             140 ttg gcc agt act gct act gca atc aca atc caa agg gat tgg att gtt      480
Leu Ala Ser Thr Ala Thr Ala Ile Thr Ile Gln Arg Asp Trp Ile Val
145             150             155             160 gtt gtt gca gga gaa gac aga agc aaa cta gca aat atg aat gcc aca      528
Val Val Ala Gly Glu Asp Arg Ser Lys Leu Ala Asn Met Asn Ala Thr
                165             170             175 ata cga agg att gac cag tta acc aac atc tta gcc ccc atg gct gtt      576
Ile Arg Arg Ile Asp Gln Leu Thr Asn Ile Leu Ala Pro Met Ala Val
            180             185             190 ggc cag att atg aca ttt ggc tcc cca gtc atc ggc tgt ggc ttt att      624
Gly Gln Ile Met Thr Phe Gly Ser Pro Val Ile Gly Cys Gly Phe Ile
        195             200             205 tcg gga tgg aac ttg gta tcc atg tgc gtg gag tac gtc ctg ctc tgg      672
Ser Gly Trp Asn Leu Val Ser Met Cys Val Glu Tyr Val Leu Leu Trp
    210             215             220 aag gtt tac cag aaa acc cca gct cta gct gtg aaa gct ggt ctt aaa      720
Lys Val Tyr Gln Lys Thr Pro Ala Leu Ala Val Lys Ala Gly Leu Lys
225             230             235             240 gaa gag gaa act gaa ttg aaa cat ctg aat tta cac aaa gat act gag      768
Glu Glu Glu Thr Glu Leu Lys His Leu Asn Leu His Lys Asp Thr Glu
                245             250             255 cca aaa ccc ctg gag gga act cat cta atg ggt gtg aaa gac tct aac      816
Pro Lys Pro Leu Glu Gly Thr His Leu Met Gly Val Lys Asp Ser Asn
            260             265             270 atc cat gag ctt gaa cat gag caa gag cct act tgt gcc tcc cag atg      864
Ile His Glu Leu Glu His Glu Gln Glu Pro Thr Cys Ala Ser Gln Met
        275             280             285 gct gag ccc ttc cgt acc ttc cga gat gga tgg gtc tcc tac tac aac      912
Ala Glu Pro Phe Arg Thr Phe Arg Asp Gly Trp Val Ser Tyr Tyr Asn
    290             295             300 cag cct gtg ttt ctg gct ggc atg ggt ctt gct ttc ctt tat atg act      960
Gln Pro Val Phe Leu Ala Gly Met Gly Leu Ala Phe Leu Tyr Met Thr
305             310             315             320 gtc ctg ggc ttt gac tgc atc acc aca ggg tac gcc tac act cag gga     1008
Val Leu Gly Phe Asp Cys Ile Thr Thr Gly Tyr Ala Tyr Thr Gln Gly
                325             330             335 ctg agt ggt tcc atc ctc agt att ttg atg gga gca tca gct ata act     1056
Leu Ser Gly Ser Ile Leu Ser Ile Leu Met Gly Ala Ser Ala Ile Thr
            340             345             350
```

```
gga ata atg gga act gta gct ttt act tgg cta cgt cga aaa tgt ggt      1104
Gly Ile Met Gly Thr Val Ala Phe Thr Trp Leu Arg Arg Lys Cys Gly
        355                 360                 365 ttg gtt cgg aca ggt ctg atc tca gga ttg gca cag ctt tcc tgt ttg      1152
Leu Val Arg Thr Gly Leu Ile Ser Gly Leu Ala Gln Leu Ser Cys Leu
    370                 375                 380 atc ttg tgt gtg atc tct gta ttc atg cct gga agc ccc ctg gac ttg      1200
Ile Leu Cys Val Ile Ser Val Phe Met Pro Gly Ser Pro Leu Asp Leu
385                 390                 395                 400 tcc gtt tct cct ttt gaa gat atc cga tca agg ttc att caa gga gag      1248
Ser Val Ser Pro Phe Glu Asp Ile Arg Ser Arg Phe Ile Gln Gly Glu
                405                 410                 415 tca att aca cct acc aag ata cct gaa att aca act gaa ata tac atg      1296
Ser Ile Thr Pro Thr Lys Ile Pro Glu Ile Thr Thr Glu Ile Tyr Met
            420                 425                 430 tct aat ggg tct aat tct gct aat att gtc ccg gag aca agt cct gaa      1344
Ser Asn Gly Ser Asn Ser Ala Asn Ile Val Pro Glu Thr Ser Pro Glu
        435                 440                 445 tct gtg ccc ata atc tct gtc agt ctg ctg ttt gca ggc gtc att gct      1392
Ser Val Pro Ile Ile Ser Val Ser Leu Leu Phe Ala Gly Val Ile Ala
    450                 455                 460 gct aga atc ggt ctt tgg tcc ttt gat tta act gtg aca cag ttg ctg      1440
Ala Arg Ile Gly Leu Trp Ser Phe Asp Leu Thr Val Thr Gln Leu Leu
465                 470                 475                 480 caa gaa aat gta att gaa tct gaa aga ggc att ata aat ggt gta cag      1488
Gln Glu Asn Val Ile Glu Ser Glu Arg Gly Ile Ile Asn Gly Val Gln
                485                 490                 495 aac tcc atg aac tat ctt ctt gat ctt ctg cat ttc atc atg gtc atc      1536
Asn Ser Met Asn Tyr Leu Leu Asp Leu Leu His Phe Ile Met Val Ile
            500                 505                 510 ctg gct cca aat cct gaa gct ttt ggc ttg ctc gta ttg att tca gtc      1584
Leu Ala Pro Asn Pro Glu Ala Phe Gly Leu Leu Val Leu Ile Ser Val
        515                 520                 525 tcc ttt gtg gca atg ggc cac att atg tat ttc cga ttt gcc caa aat      1632
Ser Phe Val Ala Met Gly His Ile Met Tyr Phe Arg Phe Ala Gln Asn
    530                 535                 540 act ctg gga aac aag ctc ttt gct tgc ggt cct gat gca aaa gaa gtt      1680
Thr Leu Gly Asn Lys Leu Phe Ala Cys Gly Pro Asp Ala Lys Glu Val
545                 550                 555                 560 agg aag gaa aat caa gca aat aca tct gtt gtt tga                      1716
Arg Lys Glu Asn Gln Ala Asn Thr Ser Val Val
                565                 570

<210> SEQ ID NO 8
<211> LENGTH: 571
<212> TYPE: PRT
<213> ORGANISM: Homo sapiens

<400> SEQUENCE: 8

Met Thr Arg Ala Gly Asp His Asn Arg Gln Arg Gly Cys Cys Gly Ser
1               5                   10                  15

Leu Ala Asp Tyr Leu Thr Ser Ala Lys Phe Leu Leu Tyr Leu Gly His
            20                  25                  30

Ser Leu Ser Thr Trp Gly Asp Arg Met Trp His Phe Ala Val Ser Val
        35                  40                  45

Phe Leu Val Glu Leu Tyr Gly Asn Ser Leu Leu Leu Thr Ala Val Tyr
    50                  55                  60

Gly Leu Val Val Ala Gly Ser Val Leu Val Leu Gly Ala Ile Ile Gly
65                  70                  75                  80
```

-continued

```
Asp Trp Val Asp Lys Asn Ala Arg Leu Lys Val Ala Gln Thr Ser Leu
             85                  90                  95
Val Val Gln Asn Val Ser Val Ile Leu Cys Gly Ile Ile Leu Met Met
            100                 105                 110
Val Phe Leu His Lys His Glu Leu Leu Thr Met Tyr His Gly Trp Val
            115                 120                 125
Leu Thr Ser Cys Tyr Ile Leu Ile Thr Ile Ala Asn Ile Ala Asn
            130                 135                 140
Leu Ala Ser Thr Ala Thr Ala Ile Thr Ile Gln Arg Asp Trp Ile Val
145                 150                 155                 160
Val Val Ala Gly Glu Asp Arg Ser Lys Leu Ala Asn Met Asn Ala Thr
            165                 170                 175
Ile Arg Arg Ile Asp Gln Leu Thr Asn Ile Leu Ala Pro Met Ala Val
            180                 185                 190
Gly Gln Ile Met Thr Phe Gly Ser Pro Val Ile Gly Cys Gly Phe Ile
            195                 200                 205
Ser Gly Trp Asn Leu Val Ser Met Cys Val Glu Tyr Val Leu Leu Trp
            210                 215                 220
Lys Val Tyr Gln Lys Thr Pro Ala Leu Ala Val Lys Ala Gly Leu Lys
225                 230                 235                 240
Glu Glu Glu Thr Glu Leu Lys His Leu Asn Leu His Lys Asp Thr Glu
            245                 250                 255
Pro Lys Pro Leu Glu Gly Thr His Leu Met Gly Val Lys Asp Ser Asn
            260                 265                 270
Ile His Glu Leu Glu His Glu Gln Glu Pro Thr Cys Ala Ser Gln Met
            275                 280                 285
Ala Glu Pro Phe Arg Thr Phe Arg Asp Gly Trp Val Ser Tyr Tyr Asn
            290                 295                 300
Gln Pro Val Phe Leu Ala Gly Met Gly Leu Ala Phe Leu Tyr Met Thr
305                 310                 315                 320
Val Leu Gly Phe Asp Cys Ile Thr Thr Gly Tyr Ala Tyr Thr Gln Gly
            325                 330                 335
Leu Ser Gly Ser Ile Leu Ser Ile Leu Met Gly Ala Ser Ala Ile Thr
            340                 345                 350
Gly Ile Met Gly Thr Val Ala Phe Thr Trp Leu Arg Arg Lys Cys Gly
            355                 360                 365
Leu Val Arg Thr Gly Leu Ile Ser Gly Leu Ala Gln Leu Ser Cys Leu
            370                 375                 380
Ile Leu Cys Val Ile Ser Val Phe Met Pro Gly Ser Pro Leu Asp Leu
385                 390                 395                 400
Ser Val Ser Pro Phe Glu Asp Ile Arg Ser Arg Phe Ile Gln Gly Glu
            405                 410                 415
Ser Ile Thr Pro Thr Lys Ile Pro Glu Ile Thr Thr Glu Ile Tyr Met
            420                 425                 430
Ser Asn Gly Ser Asn Ser Ala Asn Ile Val Pro Glu Thr Ser Pro Glu
            435                 440                 445
Ser Val Pro Ile Ile Ser Val Ser Leu Leu Phe Ala Gly Val Ile Ala
            450                 455                 460
Ala Arg Ile Gly Leu Trp Ser Phe Asp Leu Thr Val Thr Gln Leu Leu
465                 470                 475                 480
Gln Glu Asn Val Ile Glu Ser Glu Arg Gly Ile Ile Asn Gly Val Gln
            485                 490                 495
```

```
Asn Ser Met Asn Tyr Leu Leu Asp Leu Leu His Phe Ile Met Val Ile
            500                 505                 510

Leu Ala Pro Asn Pro Glu Ala Phe Gly Leu Leu Val Leu Ile Ser Val
        515                 520                 525

Ser Phe Val Ala Met Gly His Ile Met Tyr Phe Arg Phe Ala Gln Asn
    530                 535                 540

Thr Leu Gly Asn Lys Leu Phe Ala Cys Gly Pro Asp Ala Lys Glu Val
545                 550                 555                 560

Arg Lys Glu Asn Gln Ala Asn Thr Ser Val Val
                565                 570

<210> SEQ ID NO 9
<211> LENGTH: 20
<212> TYPE: DNA
<213> ORGANISM: Homo sapiens
<220> FEATURE:
<221> NAME/KEY: polymerase chain reaction primer
<222> LOCATION: (1)..(20)
<223> OTHER INFORMATION: 5' PCR primer. Exon 1

<400> SEQUENCE: 9
ggtgctatct ccagttcctt                                              20

<210> SEQ ID NO 10
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: 3' PCR primer. Exon1

<400> SEQUENCE: 10
gttcacagca gagccacatt                                              20

<210> SEQ ID NO 11
<211> LENGTH: 25
<212> TYPE: DNA
<213> ORGANISM: Homo sapiens
<220> FEATURE:
<221> NAME/KEY: misc_feature
<222> LOCATION: (1)..(25)
<223> OTHER INFORMATION: 5' PCR primer. Exon 2

<400> SEQUENCE: 11
cagctcatta agtgactacc atcgc                                        25

<210> SEQ ID NO 12
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: 3' PCR primer. exon 2

<400> SEQUENCE: 12
ggcttaatac aactggctag aacg                                         24

<210> SEQ ID NO 13
<211> LENGTH: 23
<212> TYPE: DNA
<213> ORGANISM: Homo sapiens
<220> FEATURE:
<221> NAME/KEY: misc_feature
<222> LOCATION: (1)..(23)
```

```
<223> OTHER INFORMATION: 5' PCR primer. Exon 3

<400> SEQUENCE: 13
cataatgtag ccaggaagtg ccc                                              23

<210> SEQ ID NO 14
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: 3' PCR primer. Exon 3

<400> SEQUENCE: 14
tccagaggtg gtgccatcta ag                                               22

<210> SEQ ID NO 15
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: 5' PCR primer. Exon 4

<400> SEQUENCE: 15
gagacatttt gatgtaatgt acac                                             24

<210> SEQ ID NO 16
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: 3' PCR primer. Exon 4

<400> SEQUENCE: 16
ctaccagata ttcaattttc tgcc                                             24

<210> SEQ ID NO 17
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: 5' PCR primer. Exon 5

<400> SEQUENCE: 17
ccaccaaaga ctattttaaa ctgc                                             24

<210> SEQ ID NO 18
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: 3' PCR primer. Exon 5

<400> SEQUENCE: 18
tcaccaccga tttaaagtga atcc                                             24

<210> SEQ ID NO 19
<211> LENGTH: 23
```

```
<212> TYPE: DNA
<213> ORGANISM: Homo sapiens
<220> FEATURE:
<221> NAME/KEY: misc_feature
<222> LOCATION: (1)..(23)
<223> OTHER INFORMATION: 5' PCR primer. Exon 6 .

<400> SEQUENCE: 19
gtattgtgta aatgggcagt ctc                                              23

<210> SEQ ID NO 20
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: 3' PCR primer.Exon 6

<400> SEQUENCE: 20
ccccactggt aataaaacct g                                                21

<210> SEQ ID NO 21
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: 5' PCR primer. Exon  7

<400> SEQUENCE: 21 ggctttatt tctacatgtc ctcc                                              24

<210> SEQ ID NO 22
<211> LENGTH: 23
<212> TYPE: DNA
<213> ORGANISM: Homo sapiens
<220> FEATURE:
<221> NAME/KEY: misc_feature
<222> LOCATION: (1)..(23)
<223> OTHER INFORMATION: 3' PCR primer. Exon 7

<400> SEQUENCE: 22
acatttaggg aacatttcag atc                                              23

<210> SEQ ID NO 23
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: 5' PCR primer. Exon 8

<400> SEQUENCE: 23
aaggtgactt aaagacagtc aggc                                             24

<210> SEQ ID NO 24
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: 3' PCR primer. Exon 8

<400> SEQUENCE: 24
```

-continued

```
gctgacttag gtttcctaaa cagc                                              24

<210> SEQ ID NO 25
<211> LENGTH: 10
<212> TYPE: DNA
<213> ORGANISM: Homo sapiens
<220> FEATURE:
<221> NAME/KEY: misc_feature
<222> LOCATION: (1)..(10)
<223> OTHER INFORMATION: oligonucleotide comprising the polymorphism at
      nt 238

<400> SEQUENCE: 25
atcagtgact                                                              10

<210> SEQ ID NO 26
<211> LENGTH: 10
<212> TYPE: DNA
<213> ORGANISM: Homo sapiens
<220> FEATURE:
<221> NAME/KEY: misc_feature
<223> OTHER INFORMATION: oligonucleotide comprising the polymorphism at
      nt 521.

<400> SEQUENCE: 26
gatgattgcc                                                              10

<210> SEQ ID NO 27
<211> LENGTH: 10
<212> TYPE: DNA
<213> ORGANISM: Homo sapiens
<220> FEATURE:
<221> NAME/KEY: misc_feature
<222> LOCATION: (1)..(10)
<223> OTHER INFORMATION: oligonucleotide comprising the polymorphism at
      nt 744

<400> SEQUENCE: 27
gaaacatctg                                                              10

<210> SEQ ID NO 28
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: X different from glycine

<400> SEQUENCE: 28

Ile Ile Xaa Asp Trp
1               5

<210> SEQ ID NO 29
<211> LENGTH: 5
<212> TYPE: PRT
<213> ORGANISM: homo sapiens
<220> FEATURE:
<221> NAME/KEY: MISC_FEATURE
<222> LOCATION: (1)..(5)
<223> OTHER INFORMATION: X different form asparagine

<400> SEQUENCE: 29

Asn Met Xaa Ala Thr
1               5

<210> SEQ ID NO 30
<211> LENGTH: 5
```

```
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: X different from glutamine

<400> SEQUENCE: 30

Leu Lys Xaa Leu Asn
1               5
```